United States Patent
Harel-Bellan et al.

(10) Patent No.: US 7,371,735 B2
(45) Date of Patent: May 13, 2008

(54) INHIBITOR OLIGONUCLEOTIDES AND THEIR USE FOR SPECIFIC REPRESSION OF A GENE

(75) Inventors: Annick Harel-Bellan, Paris (FR); Slimane Ait-Si-Ali, Villejuif (FR); Florence Cabon-Georget, Vitry sur Seine (FR); Anne Chauchereau, Fontenay-aux-Roses (FR); Francois Dautry, Paris (FR)

(73) Assignee: Centre National de la Recherche Scientifique-CNRS (FR)

( * ) Notice: Subject to any disclaimer, the term of this patent is extended or adjusted under 35 U.S.C. 154(b) by 41 days.

(21) Appl. No.: 10/494,800

(22) PCT Filed: Nov. 8, 2002

(86) PCT No.: PCT/FR02/03843

§ 371 (c)(1),
(2), (4) Date: Sep. 27, 2004

(87) PCT Pub. No.: WO03/040366

PCT Pub. Date: May 15, 2003

(65) Prior Publication Data

US 2005/0215497 A1    Sep. 29, 2005

(30) Foreign Application Priority Data

Nov. 9, 2001    (FR) ................... 01 14549
Apr. 10, 2002   (FR) ................... 02 04474

(51) Int. Cl.
*A01N 43/04*    (2006.01)
*A61K 31/70*    (2006.01)
*C07H 21/04*    (2006.01)
*C12Q 1/68*     (2006.01)
*C12N 5/00*     (2006.01)

(52) U.S. Cl. ............... 514/44; 536/23.1; 536/24.5; 435/6; 435/375

(58) Field of Classification Search ............... 514/44; 536/24.5
See application file for complete search history.

(56) References Cited

FOREIGN PATENT DOCUMENTS

| WO | WO 00/20432 A | 4/2000 |
| WO | WO 00/66724 A | 11/2000 |
| WO | WO 01/36646 A | 5/2001 |
| WO | WO 01/75164 A | 10/2001 |
| WO | WO 02/055692 A | 7/2002 |
| WO | WO 03/070969 A | 8/2003 |

OTHER PUBLICATIONS

Kennerdell et al., Heritable gene silencing in Drosophila using double-stranded RNA, Jul. 2000, Nature Biotechnology, vol. 17, pp. 896-898.*
Opalinska et al., Nucleic-acid therapeutics: Basic principles and recent applications, Jul. 2002, Nature Reviews Drug Discovery, vol. 1, pp. 503-514.*
Tuschl et al., Samll interfering RNAs: A revolutionary tool for the analysis of gene function and gene therapy, Jun. 2002, Molecular Interventions, vol. 2, pp. 158-167.*
Definition of "prevent", Merriam-Webster Online Dictionary, http://m-w.com/dictionary/prevent, p. 1 of 1 is enclosed, Accessed and printed on Nov. 24, 2006.*
Sayda M. Elbashir et al., *RNA interference is mediated by 21- and 22-nucleotide RNAs*, Genes & Development, vol. 15, No. 2, Jan. 15, 2001, pp. 188-200 (XP002206453).
Sayda M. Elbashir et al., *Duplexes of 21-nucleotide RNAs mediate RNA interference in cultured mammalian cells*, NATURE, vol. 411, No. 6836, May 24, 2001, pp. 494-498 (XP002206451).
Sayda M. Elbashir et al., *Knockdown of mammalian gene expression using small interfering RNAs*, Biology of the Cell, vol. 93, No. 3-4, Oct. 2001, pp. 259 (XP002206454).
Sayda M. Elbashir et al., *Functional anatomy of siRNAs for mediating efficient RNAi in Drosophila melanogaster embryo lysate*, The EMBO Journal, vol. 20, No. 23, Dec. 3, 2001, pp. 6877-6888 (XP0002225998).
Takashi Futami et al., *Induction of apoptosis in HeLa cells with siRNA expression vector targeted against bel-2*, Nucleic Acids Research, Supplement, No. 2, pp. 251-252 (XP002264267), Database Medline Accession No. NLM12903200.

* cited by examiner

*Primary Examiner*—Jon E. Angell
*Assistant Examiner*—Dana Shin
(74) *Attorney, Agent, or Firm*—DLA Piper US LLP

(57) ABSTRACT

A method of treating a disease resulting from the expression of a harmful gene is described. The method includes the step of administering a therapeutically effective amount of a pharmaceutical composition having at least one double stranded oligonucleotide including two complementary oligonucleotide sequences forming a hybrid. Each oligonucleotide sequence comprises at one of their 3' or 5' ends one to five unpaired nucleotides forming single-strand ends extending beyond the hybrid. One of the oligonucleotide sequences is substantially complementary to a target sequence belonging to a DNA or messenger RNA molecule of a gene coding a mutated or nonmutated androgen receptor.

1 Claim, 14 Drawing Sheets

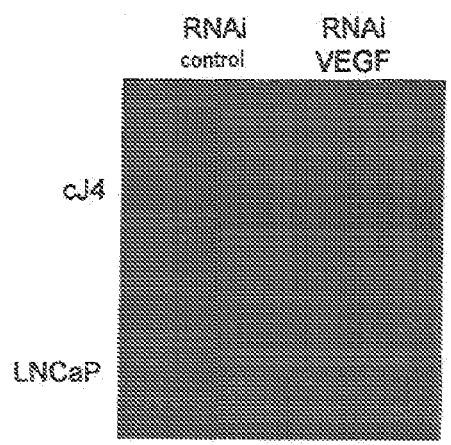
Fig. 2 A
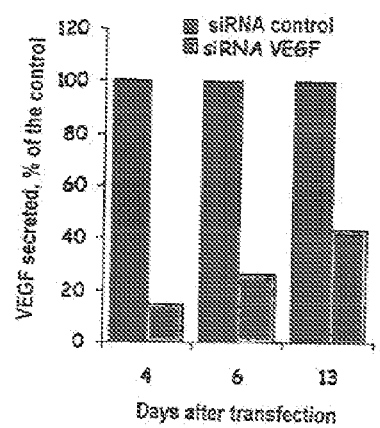
Fig. 2 B
Fig. 2 C
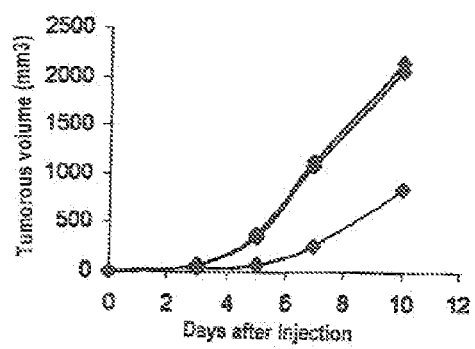
Fig. 2 D
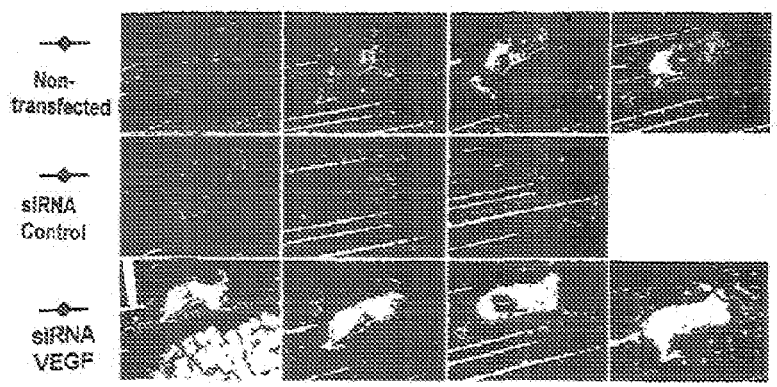

Fig. 5 A

```
   1 atggaggagc cgcagtcaga ccctagcgtc gagcccctc tgagtcagga aacattttca
  61 gacctatgga aactacttcc tgaaaacaac gttctgtccc ccttgccgtc ccaagcaatg
 121 gatgatttga tgctgtcccc ggacgatatt gaacaatggt tcactgaaga cccaggtcca
 181 gatgaagctc ccagaatgcc agaggctgct ccccccgtgg cccatgcacc agcagctcct
 241 acaccggcgg ccctgcacc agcccctcc tggccctgt catcttctgt ccttccag
 301 aaaacctacc agggcagcta cggtttccgt ctgggcttct tgcattctgg gacagccaag
 361 tctgtgactt gcacgtactc ccctgccctc aacaagatgt ttgccaact ggccaagacc
 421 tgccctgtgc agctgtgggt tgattccaca cccccgcccg gcaccgcgt ccgcgccatg
 481 gccatctaca agcagtcaca gcacatgacg gaggttgtga ggcgctgccc ccaccatgag
 541 cgctgctcag atagcgatgg tctggcccct cctcagcatc ttatccgagt ggaaggaaat
 601 ttgcgtgtgg agtatttgga tgacagaaac acttttcgac atagtgtggt ggtgccctat
 661 gagccgcctg aggttggctc tgactgtacc accatccact acaactacat gtgtaacagt
 721 tcctgcatgg gcggcatgaa ccggaggccc atcctcacca tcatcacact ggaagactcc
 781 agtggtaatc tactgggacg gaacagcttt gaggtgcgtg tttgtgcctg tcctgggaga
 841 gaccggcgca cagaggaaga gaatctccgc aagaaagggg agcctcacca cgagctgccc
 901 ccaggagca ctaagcgagc actgcccaac aacaccagct cctctccca gccaaagaag
 961 aaaccactgg atggagaata tttcaccctt cagatccgtg ggcgtgagcg cttcgagatg
1021 ttccgagagc tgaatgaggc cttggaactc aaggatgccc aggctgggaa ggagccaggg
1081 gggagcaggg ctcactccag ccacctgaag tccaaaaagg gtcagtctac ctcccgccat
1141 aaaaaactca tgttcaagac agaagggcct gactcagact ga
```

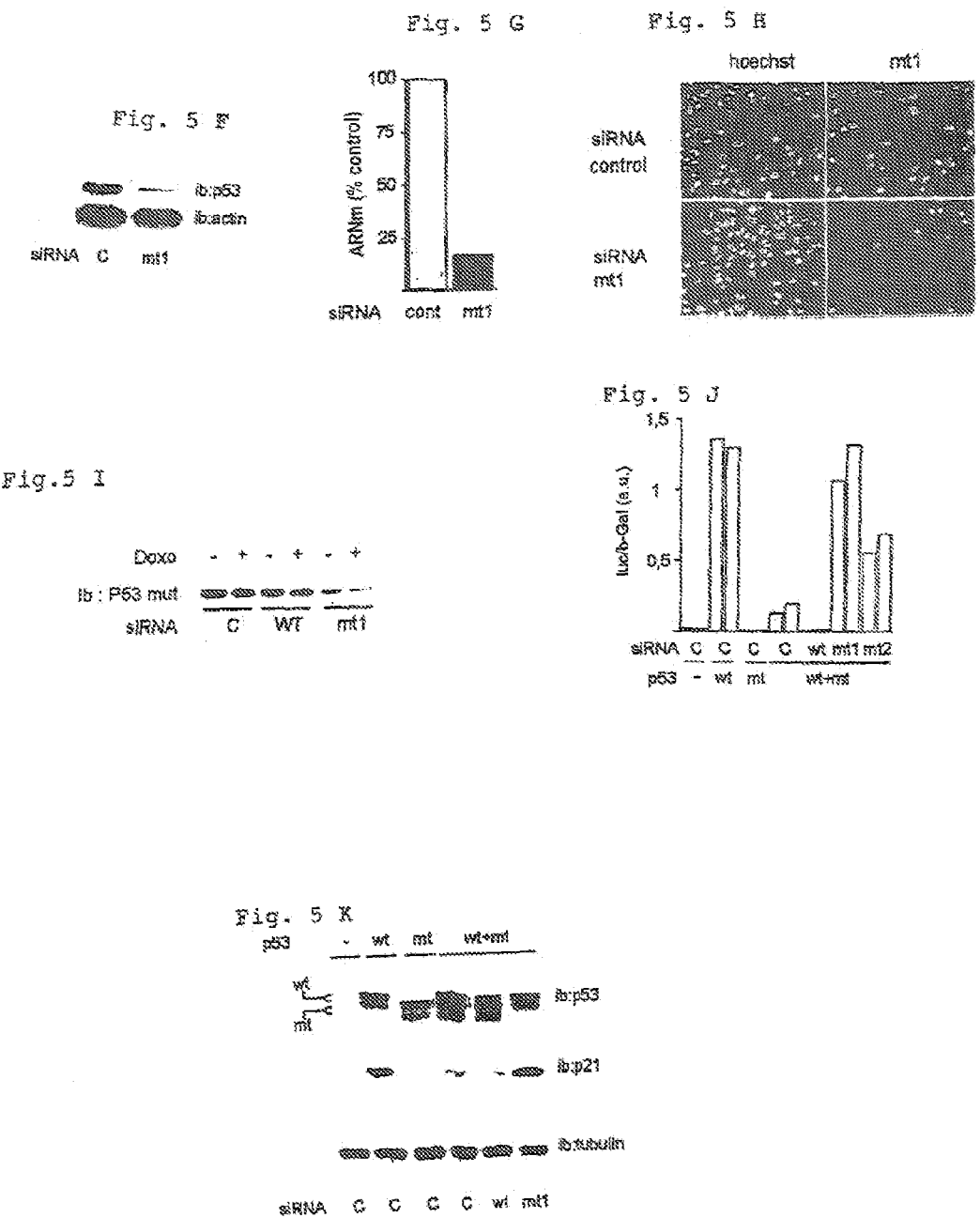

Fig. 6 A

```
   1 actacaataa ttcatgtata aaactaaggg cgtaaccgaa atcggttgaa ccgaaaccgg
  61 ttagtataaa agcagacatt ttatgcacca aaagagaact gcaatgtttc aggaccgaca
 121 ggagcgaccc agaaagttac cacagttatg cacagagctg caaacaacta tacatgatat
 181 aatattagaa tgtgtgtact gcaagcaaca gttactgcga cgtgaggtat atgactttgc
 241 ttttcgggat ttatgcatag tatatagaga tgggaatcca tatgctgtat gtgataaatg
 301 tttaaagttt tattctaaaa ttagtgagta tagacattat tgttatagtt tgtatggaac
 361 aacattegaa cagcaataca acaaaccgtt gtgtgatttg ttaattaggt gtattaactg
 421 tcaaaagcca ctgtgtcctg aagaaaagca aagacatctg gacaaaagc aaagattcca
 481 taatataagg ggtcggtgga ccggtcgatg tatgtcttgt tgcagatcat caagaacacg
 541 tagagaaacc cagctgtaat catgcatgga gatacaccta cattgcatga atatatgtta
 601 gattgcaac cagagacaac tgatctctac tgttatgagc aattaaatga cagctcagag
 661 gaggaggatg aaatagatgg tcagctgga caagcagaac cggacagagc tcattacaat
 721 attgtaacct tttgttgcaa gtgtgactct acgcttcggt tgtgcgtaca aagcacacac
 781 gtagacattc gtactttgga agacctgtta atgggcacac taggaattgt gtgcccatc
 841 tgttctcaga aaccataatc taccatgct gatcctgcag gtaccaatgg ggaagagggt
 901 acgggatgta atggatggtt ttatgtagag gctgtagtgg aaaaaaaaac aggggatggt
 961 atatcagatg acgagaacga aaatgacagt gatacaggtg aagatttggt agatttata
1021 gtaaatgata atgattattt aacacaggca gaaacagaga cagcacatgc gttgtttact
1081 gcacaggaag caaaacaaca tagagatgca gtacaggttc taaaacgaaa gtatttggta
1141 gtccacttag tgatattagt ggatgtgtag acaataatgt tagtcctaga ttaaaagcta
1201 tatgtataga aaacaaagt agagctgcaa aaggagatt atttgaaagc gaagacagcg
1261 ggtatggcaa tactgaagtg gaaactcagc agatgttaca ggtagaaggg cgccatgaga
1321 ctgaaacacc atgtagtcag tatagtggtg gaagtggggg tggttgcagt cagtacagta
1381 gtggaagtgg gggagagggt gttagtgaaa gacacactat atgccaaaca ccacttacaa
1441 atattttaaa tgtactaaaa actagtaatg caaaggcagc aatgttagca aaatttaaag
1501 agttatacgg ggtgagtttt tcagaattag taagaccatt taaaagtaat aaatcaacgt
1561 gttgcgattg gtgtattgct gcatttggac ttacacccag tatagctgac agtataaaaa
1621 cactattaca acaatattgt ttatatttac acattcaaag tttagcatgt tcatggggaa
1681 tggttgtgtt actattagta agatataaat gtggaaaaaa tagagaaaca attgaaaaat
1741 tgctgtctaa actattatgt gtgtctccaa tgtgtatgat gatagagcct ccaaaattgc
1801 gtagtacagc agcagcatta tattggtata aaacaggtat atcaaatatt agtgaagtgt
1861 atggagacac gccagaatgg atacaaagac aaacagtatt acaacatagt tttaatgatt
1921 gtacattga attatcacag atggtacaat gggcctacga taatgacata gtagacgata
1981 gtgaaattgc atataaatat gcacaattgg cagacactaa tagtaatgca agtgcctttc
2041 taaaagtaa ttcacaggca aaaattgtaa aggattgtgc aacaatgtgt agacattata
2101 aacgagcaga aaaaaacaa atgagtatga gtcaatggat aaaatataga tgtgataggg
2161 tagatgatgg aggtgattgg aagcaaattg ttatgttttt aagtgatcaa ggtgtagagt
2221 ttatgtcatt tttaactgca ttaaaagat ttttgcaagg catacctaaa aaaaattgca
2281 tattactata tggtgcagct aacacaggta aatcattatt tggtatgagt cttaatgaaat
2341 ttctgcaagg gtctgtaata tgttttgtaa attctaaaag ccattttggg ttacaaccat
2401 tagcagatgc caaaataggt atgttagatg atgtacagt gccctgttgg aactacatag
2461 atgacaattt aagaaatgca ttggatggaa atttagtttc tatggatgta aagcatagac
2521 cattggtaca actaaaatgc cctccattat teattacatc taacattaat gctggtacag
2581 attctaggtg gccttattta cataatagat tgtggtgtt tacattcct aatgagttc
2641 catttgacga aaacggaaat ccagtgtatg agttaatga taagaactgg aaatcctttt
2701 tctcaaggc gtggtccaga ttaagtttgc acgaggacga ggacaaggaa aacgatggag
2761 actcttgcc aacgtttaaa tgtgtgtcag gacaaaatac taacacatta tgaaaatgat
2821 agtacagcc tacgtgacca tatagactat tggaaacaca tgcgcctaga atgtgctatt
2881 tattacaagg ccagagaaat gggatttaaa catattaacc accagtggt gccaacactg
2941 gctgtatcaa agaataaagc attacaagca attgaactgc aactaacgtt agaaacaata
3001 tataactcac aatatagtaa tgaaaagtgg acattacaag acgttagct tgaagtgtat
3061 ttaactgcac caacaggatg tataaaaaa catggatata cagtggaagt gcagtttgat
3121 ggagacatat gcaatacaat gcattataca aactggacac atatatatat ttgtgaagaa
3181 gcatcagtaa ctgtggtaga gggtcaagtt gactatatg gttatatta tgttcatgaa
3241 ggaatacgaa catatttgt gcagtttaaa gatgatgcag aaaaatatag taaaataaa
3301 gtatgggaag ttcatgcggg tggtcaggta atatatgtc ctacatctgt gttagcagc
3361 aacgaagtat cctctcctga aattattagg cagcacttgg ccaaccccc cgcgcgacc
3421 catccaaag cgtcgcctt gggcaccgaa gaaacacaga cgactatcca gcgaccaaga
3481 tcagagccag acaccggaaa ccctgccac accactaagt tgttgcacag agactcagtg
3541 gacagtgctc caatcctcac tgcatttaac agctcacaca aaggacggat taactgtaat
3601 agtaacacta cacccatagt acatttaaaa ggtgatgcta atactttaaa atgtttaaga
3661 tatagattta aaagcattg tacattgtat actgcagtgt cgtctacatg gcattggaca
3721 ggacataatg taaacataaa aagtgcaatt gttacactta catatgatag tgaatggcaa
3781 cgtgaccaat ttttgtctca agttaaaata ccaaaaacta ttacagtgtc tactggattt
3841 atgtctatat gacaaatctt gatactgcat ccacaacatt actggcgtga ttttttgcttt
3901 gctttgtgtg cttttgtgtg tctgcctatt aatacgtccg ctgctttgt ctgtgtctac
3961 atacacatca ttaataatat tggtattact attgtggata acagcagcct ctgcgtttag
```

Fig. 6 A (continued)

```
4021 gtgttttatt gtatatatta tatttgttta tatcbcatta tttttaatac atacacatgc
4081 acgcttttta attacataat gtatatgtac ataatgtaat tgttacatat aattgttgta
4141 taccataact tactattttt tcttttttat tttcatatat aattttttt tttgtttgtt
4201 tgtttgtttt ttaataaact gttattactt aacaatgcga cacaaacgtt ctgcaaaacg
4261 cacaaaacgt gcatcggcta cccaacttta taaaacatgc aaacaggcag gtacatgtcc
4321 acctgacatt atacctaagg ttgaagcaaa aactattgct gaacaaatat tacaatatgg
4381 aagtatgggt gtattttttg gtgggttagg aattggaaca gggtcgggta caggcggacg
4441 cactgggtat attccattgg gaacaaggcc tcccacagct acagatacac ttgctcctgt
4501 aagacccct ttaacagtag atcctgtggg cccttctgat cctctatag tttctttagt
4561 ggaagaaact agttttattg atgctgtgc accaacatct gtaccttcca ttccccaga
4621 tgtatcagga tttagtatta ctacttcaac tgataccaca cctgctatat tagatattaa
4691 taatactgtt actactgtta ctacacataa taatcccact ttcactgacc catctgtatt
4741 gcagcctcca acacctgcag aaactggagg gcatttaca ctttcatcat ccactattag
4801 tacacataat tatgaagaaa ttcctatgga tacattatt gttagcacaa accctaacac
4861 agtaactagt agcacaccca taccagggtc tcgcccagtg gcacgcctag gattatatag
4921 tcgcacaaca caacaggtta aagttgtaga cctgctttt gtaaccactc ccactaaact
4981 tattacatat gataatcctg catatgaagg tatagatgtg gataatacat tatattttc
5041 tagtaatgat aatagtatta atatagctcc agatcctgac ttttggata tagttgcttt
5101 acataggcca gcattaacct ctaggcgtac tggcattagg tacagtagaa ttggtaataa
5161 acaaacacta cgtactgta gtggaaaatc tataggtgct aagtacatt attattatga
5221 tttaagtact attgatcctg cagaagaaat agaattacaa actataacac cttctacata
5281 tactaccact toacatgcag cctcacctac ttctattaat aatggattat atgatattta
5341 tgcagatgac tttattacag atacttctac aaccccggta ccatctgtac cctctacatc
5401 tttatcaggt tatattcctg caaatacaac aattccttt ggtggtgcat acaatattcc
5461 tttagtatca ggtcctgata taccattaa tataactgac caagctcctt cattaattcc
5521 tatagttcca gggtctccac aatatacaat tattgctgat gcaggtgact tttatttaca
5581 tcctagttat tacatgttac gaaaacgacg taaacgttta ccatattt tttcagatgt
5641 ctctttggct gcctagtgag gccactgtct acttgctcc tgtcccagta tctaaggttg
5701 taagcacgga tgaatatgtt gcacgcacaa acatatatta tcatgcagga acatccagac
5761 tacttgcagt tggacatccc tatttcta ttaaaaaacc taacaataac aaaatattag
5821 ttcctaaagt atcaggatta caatacaggg tatttagaat acatttacct gacccccaata
5881 agtttggttt tctgacacc tcattttata atccagatac acagcggctg gtttgggcct
5941 gtgtaggtgt tgaggtaggt cgtggtcagc cattaggtgt gggcattagt ggccatcctt
6001 tattaaataa attggatgac acagaaaatg ctagtgctta tgcacgaaat gcaggtgtgg
6061 ataatagaga atgtatatct atggattaca aacaaacaca attgtgttta attggttgca
6121 aaccacctat aggggaacac tggggcaaag gatcccatcg taccagtgtt gcagtaaatc
6181 caggtgattg tccaccatta gagttaataa acacagttat tcaggatggt gatatggttc
6241 atactggctt tagtgctatg gacttactta cattacaggc taacaaagt gaagttccac
6301 tggatatttg tacatctatt tgcaaatatc cagattatat taaaatggtg tcagaaccat
6361 atggcgacag cttatttttt tatttacgaa gggaaacaaat gtttgttaga catttattta
6421 ataggcgtgg tactgttggt gaaaatgtac cagacgattt atacattaaa ggctctgggt
6481 ctactgcaaa tttagccagt tcaaattatt ttcctaccc tagtggttct atggttacct
6541 ctgatgccca aatattcaat aaaccttatt ggttgttga tactacacgc acaataatg
6601 gcattgttg gggtaaccaa ctattgtta ctgttgttga agcacagggc cacaataatg
6661 tgtcattatg tgctgccata tctactcag aaactacata taaaatact aactttaagg
6721 agtacctacg acatggggag gaatatgatc tacagtttat ttttcaactg tgcaaaataa
6781 ccttaactgc agacgttatg acatacatac attctatgaa ttccactatt ttggaggact
6841 ggaattttgg tctacaacct ccccaggag gcacactaga agatttat aggtttgtaa
6901 cccaggcaat tgcttgtcaa aaacatacac ctccagcacc taaagaagat gatcccctta
6961 aaaaatacac ttttggaa gtaaattaa aggaaagtt ttctgcagac ctagatcagt
7021 ttccttagg acgcaaattt ttactacaag caggattgaa ggcaacca aaattcat
7081 taggaaacg aaagctaca cccaccacct catctaccct tacaactgct aaacgcaaaa
7141 aacgtaagct gtaagtattg tatgtatgtt gaattagtgt tgtttgttgt gtatatgttt
7201 gtatgtgctt gtatgtgctt gtaaatatta agttgtatgt gtgtttgtat gtatggtata
7261 ataaacacgt gtgtatgtgt ttttaaatgc ttgtgtaact atgtgtcat gcaacataaa
7321 taaacttatt gtttcaacac ctactaattg tgttgtggtt attcattgta tataaactat
7381 attttgctaca tcctgtttt gttttatata tactatattt tgtagcgcca ggccattttt
7441 gtagcttcaa ccgattcgg ttgcatgctt tttggcacaa aatgttttt ttaaatagt
7501 tctatgtcag caactatggt ttaaacttgt acgttcctg cttgccatgc gtgccaaatc
7561 cctgttttcc tgacctgac tgcttgccaa ccattccatt gttttttaca ctgcactatg
7621 tgcaactact gaatcactat gtacattgtg tcatataaaa taaatcacta tgcgccaacg
7681 ccttacatac cgctgttagg cacatatttt tggcttgttt taactaacct aattgcatat
7741 ttggcataag gtttaaactt ctaaggccaa ctaaatgtca cctagttca tacatgaact
7801 gtgtaaaggt tagtcataca ttgttcattt gtaaactgc acatgggtgt gtgcaaaccg
7861 attttgggtt acacatttac aagcaactta tataataata ctaa
```

Fig. 7 A
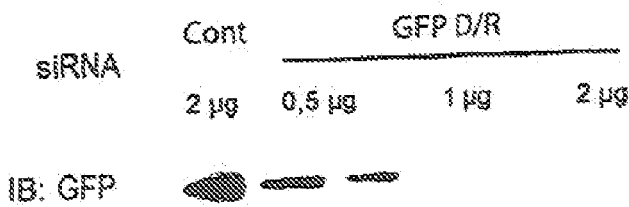
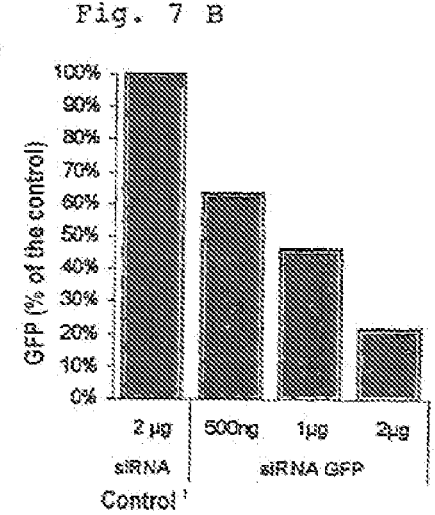
Fig. 7 B
Fig. 7 C
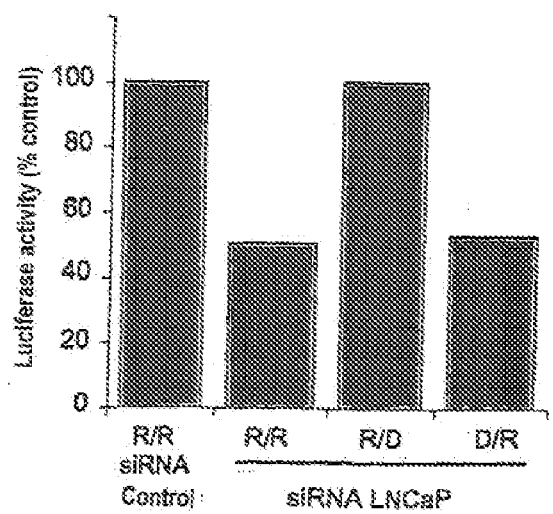

INHIBITOR OLIGONUCLEOTIDES AND THEIR USE FOR SPECIFIC REPRESSION OF A GENE

RELATED APPLICATIONS

This is a §371 of PCT/FR02/03843, filed Nov. 8, 2002 (now WO 03/040366 published May 15, 2003), which claims priority of FR 01/14549 filed Nov. 9, 2001 and FR 02/04474 filed Apr. 10, 2002.

FIELD OF THE INVENTION

This invention relates to the field of the genetic investigation and treatment of human pathologies, especially cancers and infectious diseases.

BACKGROUND

Known in the prior art are antisense oligonucleotide techniques making it possible to specifically inhibit a gene in mammal cells. These techniques are based on the introduction into cells a short oligonucleotide of DNA that is complementary to the target gene. This oligonucleotide induces the degradation of the messenger RNA (mRNA) transcribed by the target gene. Another the antisense technique comprises introducing into a cell a DNA oligonucleotide which forms a triple strand with the target gene. The formation of this triple strand represses the gene by either blocking access for activating proteins, or in more sophisticated approaches, by inducing degradation of the gene. None of these approaches appear to be based on a cellular mechanism existing in the cells of mammals, and they are not very effective. In fact, the clinical use of antisense has been reduced to a few rare cases, and it was believed that there was no possible use for oligonucleotides forming triple strands.

Interference RNA which is also designated "RNA'inh" or "RNAi" or cosuppression, has been demonstrated in plants. It was observed in plants that the introduction of a long double-strand RNA corresponding to a gene induced the specific and effective repression of the target gene. The mechanism of this interference comprises the degradation of the double-strand RNA into short oligonucleotide duplexes of 20 to 22 nucleotides.

The "RNA'inh" approach, more generally referred to according to the invention as inhibitory oligonucleotides or RNAi, is based on a cellular mechanism whose importance is underlined by its high degree of conservation since this mechanism is conserved throughout the plant and animal kingdoms and species, and has been demonstrated not only in plants but also in the worm *Caenorhabditis elegans* and yeasts, and mammals—humans and mice.

SUMMARY OF THE INVENTION

This invention relates to a method of determining the function of a gene or a family of genes implicated in a cellular process. This invention also relates to a method for repressing a harmful gene responsible for a pathology in humans or animals.

The invention also relates to active agents designed to implement the methods for determining gene function and repression of harmful genes that are responsible for a pathology in humans or animals. This invention also relates to compositions containing these active agents.

In the most general sense the embodiments of this invention utilize interference RNA, also known is "RNA'inh" or "RNAi" or cosuppression.

In one aspect, the inventors have now shown that the principles of "RNA'inh" can be applied to the genes of mammals, and more specifically to genes that play an important role in the control of the cellular destiny.

BRIEF DESCRIPTION OF THE DRAWINGS

FIG. 2A represents the immunodetection of VEGF in the cJ4 or LNCaP cells transfected by the control siRNA or a siRNA directed against VEGF.

FIG. 2B represents the quantification using ELISA of VEGF in conditioned medium of cj4 cells transfected by the control siRNA or the siRNA VEGF as a function of time after transfection.

FIG. 2C represents the growth curve in nude mice of tumors stemming from the subcutaneous injection of $10^6$ cells of cJ4 that is not transfected, transfected by the control siRNA or the siRNA VEGF.

FIG. 2D represents the appearance of the tumors on day 7 after injection of the cells.

FIG. 2E represents the immunodetection of VEGF in tumors stemming from the injection of cJ4 cells transfected with the control siRNA or the siRNA VEGF after 12 days of development in vivo.

FIG. 4A represents the detection by immunoblot of the expression of the androgen receptor 48 h after transfection of the LNCaP cells by a control siRNA or a siRNA directed against the androgen receptor (AR).

FIG. 4B represents the measurement of the activity of a reporter 4×ARE luciferase to R1881 in various clones of the line LNCaP not transfected, or transfected by control siRNA or by siRNA AR.

FIG. 4C represents the comparison of the response to R1881 of LNCaP cells that were not transfected (100%), and LNCaP cells transfected by a control siRNA, a siRNA directed against the androgen receptor (AR) or a siRNA recognizing specifically a punctiform mutation present in the androgen receptor of the line LNCaP.

FIG. 4D represents the growth in nude mice of tumors resulting from the subcutaneous injection of LNCaP cells transfected by a control siRNA or by a siRNA directed against the androgen receptor.

FIG. 4E represents the growth of LNCaP tumors in mice having received on the $40^{th}$ day after implantation of the cells an intravenous injection in the tail vein of 2 µg of siRNA directed against VEGF or of control siRNA.

FIG. 4F represents the growth of LNCaP tumors in mice having received on the 34$^{th}$ and 40$^{th}$ days after implantation of the tumor cells an intraperitoneal injection of 2 μg of siRNA directed against the androgen receptor or control siRNA.

FIG. 5A represents the sequence of human p53 protein.

FIG. 5B represents the specific, dose-dependent inhibition by the siRNAs of the expression of wild or mutant forms of p53 transfected in cells not initially expressing it.

FIG. 5C represents the specific inhibition by siRNAs of the simultaneous or not simultaneous expression of wild or mutant forms of p53 transfected in cells not initially expressing it.

FIG. 5D represents the inhibition of the expression of wild endogenous p53 or a mutant form of 53 transfected by siRNA.

FIG. 5E represents the effect of the inhibition of p53 by siRNAs on the resistance to genotoxic stress.

FIGS. 5 F, G, H and I represent the inhibition of the expression of a mutant form of p53 in the cells of a patient with Li-Fraumeni cancer syndrome at the level of the mRNA (5G) and the expression of the protein by immunoblot (GF) or in indirect immunofluorescence (5H) and the consequences on the resistance of these cells to genotoxic stress.

FIG. 5J shows the inhibition by the siRNAs specific of the dependent transfection of the wild or mutant forms of p53.

FIG. 5K shows the inhibition of the expression of one of the target genes of p53, p21, inhibitory protein of cellular proliferation, by the coexpression of mutant forms of p53 and the restoration of this expression by treatment of the cells with a siRNA inhibiting the synthesis of the mutant form of p53.

FIG. 6A represents the sequence of the HPV protein.

FIG. 6B represents the effect of inhibition by siRNAs specific of the expression of protein E6 of HPV in cells that express this virus, on the expression of p53 and p21.

FIGS. 6C and 6D represent the effect of the inhibition of the expression of the protein E6 of HPV on the cell cycle.

FIGS. 7A and 7B represent the effect of siRNAs DNA/RNA hybrids on the expression of the GFP expression by transfection of the cells.

FIG. 7C compares the effect of RNA/RNA, DNA/RNA and RNA/DNA siRNAs at constant dose on the inhibition of the transcription induced by the androgen receptor.

FIGS. 7D and 7E represent the effects of a substitution of RNA bases by DNA bases in the siRNA sequence inhibiting the synthesis of p53.

DETAILED DESCRIPTION

Figure 1:
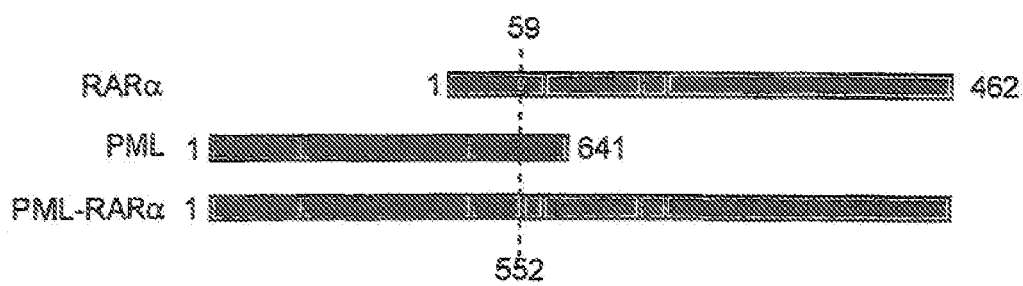
FIG. 1A is a schematic representation of the proteins RARα, PML and the associated fusion protein, PML-RARα.
FIG. 1B represents the results of transfections with an siRNA directed against PML-RARα.

In one aspect of the invention, the Applicants' demonstrate that the approach described in more detail herein is much more effective for specifically repressing genes as compared to the techniques employed in the prior art. Moreover, this approach can combine the advantages of antisense and the antigene properties. In one aspect, the Applicants have found that in plants cosuppression was effected at the post-transcriptional level on mature RNA and also at the transcriptional level, thus on the gene itself. In another aspect, the repression is transmitted from generation to generation and thus enables repression of a gene in a prolonged definitive manner.

Thus the invention has as one aspect a double-strand oligonucleotide to be used in an interference RNA (RNAi) process, that is comprised of two complementary oligonucleotide sequences each comprising at one of their 3' or 5' ends, one to five unpaired nucleotides forming single-strand ends extending beyond the hybrid, one of said oligonucleotide sequences being substantially complementary to a target sequence belonging to a target DNA or RNA molecule which it is desired to repress specifically. This DNA or RNA can be of any type, it can be, e.g., messenger or ribosomal RNA or in one aspect the DNA of a gene.

Each of the two complementary oligonucleotide sequences advantageously comprises the same 3' or 5' end with five unpaired nucleotides forming single-strand ends extending beyond the hybrid.

In one embodiment, the two oligonucleotide sequences are advantageously substantially the same size.

Because of the base-pairing law, we designate distinctions by oligonucleotide of the invention wherein one or the other of the double-strand oligonucleotide sequences of the invention that is complementary to a target sequence belonging to a DNA or RNA molecule that is specifically repressed, can be either a single or double strand.

The oligonucleotides of the invention can be of a ribonucleotide, deoxyribonucleotide or mixed nature. In a preferred embodiment the complementary oligonucleotide of the target sequence, also designated antisense strain, is comprised primarily of a ribonucleotide. The sense strain can be of a ribonucleotide, deoxyribonucleotide or mixed nature. Examples of oligonucleotides of the invention of type RNA/RNA or DNA/RNA are given in the experimental part below.

In one preferred embodiment, the RNA/RNA hybrids are more stable than the DNA/DNA or DNA/RNA hybrids and much more stable than the single-strand nucleic acids used in the antisense strategies.

The term oligonucleotide is also understood to mean a polynucleotide of 2 to 100, more generally of 5 to 50, nucleotides of the ribonucleotide, deoxyribonucleotide or mixed type.

The part of the oligonucleotide sequence that is hybridized and complementary to the target sequence preferably is of a size comprised between 15 and 25 nucleotides, most preferably from 20 to 23 nucleotides.

The double-strand oligonucleotides of the invention comprise, preferably at the 3' end of each strand, from 1 to 5 nucleotides, preferably from 2 to 3 nucleotides, and most preferably 2 nucleotides extending beyond the hybrid. These nucleotides extending beyond the hybrid can be complementary to or not complementary to the target sequence. Thus, in a particular form of implementation of the invention, the nucleotides extending beyond the hybrid are any nucleotides, e.g., thymines.

It is possible to represent a double-strand oligonucleotide of the invention in the following manner, i wherein each hyphen corresponds to a nucleotide and wherein each strand comprises at its 3' end two thymines extending beyond the hybrid:

The sequence of the oligonucleotides of the invention is substantially complementary to a target sequence belonging to a DNA or messenger RNA molecule of a gene which it is desired to repress specifically. Although preference is given to oligonucleotides perfectly complementary to the target sequence, the term "substantially complementary" is understood to refer to the fact that the oligonucleotide sequences can comprise several nucleotides mutated in relation to the target sequence as long as the repressive properties of the targeted gene are not changed. Thus, an oligonucleotide sequence of the invention can comprise from 1 to 3 mutated nucleotides.

These mutated nucleotides can thus be those extending beyond the hybrid or nucleotides within the oligonucleotide sequence.

In one aspect of the invention, an oligonucleotide of the can be a perfect hybrid or contain one or more mismatches within the double strand. Nevertheless, it is preferable that part of the oligonucleotide sequence, which is hybridized, be perfectly complementary to the target sequence whereas the nucleotides extending beyond the hybrid can be of any type and especially thymines.

The term "perfectly complementary" is understood to mean that the oligonucleotide of the invention is complementary to a sequence that belongs to a DNA or RNA of a mutated gene. The oligonucleotides of the invention can thereby enable discrimination between the sequence of the wild gene and the mutated gene present a particular value both in the analysis of the genes as well as in the therapeutic uses of the oligonucleotides of the invention.

The oligonucleotides of the invention are generally comprised of natural nucleotide bases (A, T, G, C, U) but they can also be comprised of modified nucleotides or nucleotides bearing reactive groups or bridging agents or intercalating agents that can react with the target sequence complementary to the oligonucleotide.

The oligonucleotides of the invention can be prepared by the conventional methods for the chemical or biological synthesis of oligonucleotides.

The invention also relates to oligonucleotides coupled to substances promoting or enabling their penetration, targeting, or addressing into cells. These substances can for example include lipids, proteins, polypeptides, peptides or any other natural or synthetic substance. In fact, the oligonucleotides of the invention are intended to be internalized in the cells and, advantageously in certain cases, into the nucleus of cells where they interact with nucleic acid molecules of nucleic acids bearing the oligonucleotide target sequence. Similarly, it can be of value to promote their penetration into a particular tissue such as a tumor, bone, etc.

The oligonucleotides of the invention are useful for repressing in an effective and specific manner a gene or a set of genes, thus allowing for the treatment of numerous human pathologies. They can also be used as a research tool for the investigation and the comprehension of the gene function. The invention thus, has as one object pharmaceutical compositions comprising an oligonucleotide or a set of different nucleotides and the use of these oligonucleotides, alone or coupled to transport substances, such as a drug.

The oligonucleotides can be employed in ex vivo applications, e.g., during grafting. Thus, the oligonucleotides can be transfected into the cells, especially tumor cells, which will then be injected or they can be injected into tissues. For example, the oligonucleotides can be injected into already developed tumors via the local, systemic or aerosol route, etc. with vectorization agents.

The oligonucleotides will be used at adequate concentrations in relation to the application and the form of administration employed with suitable pharmaceutical excipients. Depending on the nature of the oligonucleotides (DNA/RNA or RNA/RNA), different doses could be used in order to obtain the desired biological effect.

The oligonucleotides of the invention are also useful as diagnostic tools making it possible to establish in vitro the genetic profile of a patient on the basis of a cell sample from the patient. The implementation of the oligonucleotides of the invention in such an analysis method makes it possible to know or to anticipate the response of the cancerous cells of this patient and to establish a personalized treatment or to adjust the treatment of a patient.

The oligonucleotides of the invention present multiple advantages compared to the conventional chemotherapeutic agents:

- The RNA-RNA hybrids are more stable than the DNA-DNA or DNA-RNA hybrids and much more stable than the single-strand nucleic acids used in the antisense strategies.
- Since they constitute natural compounds, there is no fear of any immunological reactions or drug-related intolerance.
- The transfection experiments performed in the framework of the invention show a better penetration of the RNAi into the tumor cells than that obtained with plasmids. This point is essential in the case of tumor cells which are generally very difficult to transfect.
- The experiments involving systemic injection of siRNAs in vivo show a very good penetration of these molecules into the tissues.
- It is easy to mix multiple RNAi with each other in order to take as targets multiple cellular genes at the same time.

In one embodiment, the oligonucleotides of the invention and the compositions that contain them are useful for the treatment or prevention of infectious or viral diseases, such as AIDS, and the nonconventional infectious diseases, BSE and Creutzfeldt-Jakob disease. In one preferred embodiment, the oligonucleotides are suitable for treating the viral diseases at the origin of cancers. The table below presents examples of viruses implicated in cancerous pathologies in humans.

TABLE 1

| Virus | Type of associated human cancer |
|---|---|
| Hepatitis B virus (HBV) | Carcinoma of the liver |
| Epstein-Barr virus (EBV) | Burkitt's lymphoma, nasopharyngeal cancer, Hodgkins's disease, non-Hodgkins lymphoma, gastric cancer, breast cancer) |
| Human herpes virus 8 or HHV-8/KSHV | Kaposi's sarcoma (KS), primary effusion lymphoma (PEL), multicentric Castleman's disease (MCD) |
| HPV | Neck of the uterus, head, neck, skin, nasopharynx |
| Lymphocyte T virus (HTLV) | Type T leukemia |
| Hepatitis C virus (HCV) | Carcinoma of the liver |

The oligonucleotides of the invention and the compositions containing them are also useful for the treatment or prevention of diseases linked to hypervascularization such as age-linked macular degeneration, tumoral angiogenesis, diabetic retinopathies, psoriasis and rheumatoid arthritis.

The research studies performed in the framework of the invention showed that these oligonucleotides are suitable for repressing harmful genes implicated in canceration and thus most particularly useful for the treatment or prevention of cancers and oncologic diseases in general.

An ideal anticancer treatment should lead to the death of the tumor cell while avoiding resistance phenomena. Cell death can be obtained by:

Inhibition of cellular division, blocking the cell cycle,
Induction of the apoptosis of the tumor cells,
Induction of senescence,
Induction of necrosis,
Induction of differentiation. In this case, the treatment causes the cell to return to a non-cancerous state.

Thus, the invention relates in one preferred embodiment to an oligonucleotide or a set of different oligonucleotides each containing an oligonucleotide sequence complementary to a target sequence belonging to a molecule of DNA or messenger DNA of a gene whose repression induces apoptosis, or senescence or necrosis or the differentiation of the tumor cells or prevents their division or more than one of these phenomena.

Induction of apoptosis of tumor cells is based on the fact that the function of numerous cellular genes (e.g., members of the family BCL2, BCL XL) is to protect the cells from apoptosis. The loss of expression of these genes induced by RNAi enables passage into apoptosis.

Cell death can also be induced by the loss of adhesion of the cells to the matrix (anoikis). This effect can be obtained by disturbing the balance between proteases and protease inhibitors in the tumors and their stromal environment. This disturbance can also diminish the capacities of tumor cells to invade healthy tissues and metastasize. The siRNAs can thus be used to prevent the synthesis of proteins of the families of the matrix metalloproteases (MMP), membranous matrix metalloproteases, their inhibitors (TIMPs) as well as activators of the protease inhibitors such as, PAI-1, and the proteases themselves such as, urokinase.

Induction of senescence is based on the fact that normal cells can only divide a limited number of times. This number is programmed, for example circa 50 divisions for embryonic fibroblasts. Senescence can also be measured by the length of the telomeres, which get shorter as the cellular divisions advance. Below a certain size, the telomeres are no longer functional and the cell, incapable of division, enters into senescence. However, in germinal cells, this length is maintained constant by the action of an enzyme, telomerase. Telomerase is re-expressed in numerous cancers which enables the tumor cells to multiply indefinitely. A RNAi blocking the expression of telomerase would be without consequence on normal somatic cells and would lead tumor cells into senescence.

Blocking cell division also leads cells to senescence. Blockage can be obtained by inhibiting the essential cellular receptors. Depending on the nature of the cell, these receptors can belong to the class of receptors known as the growth factors (notably, EGF, SST2, PDGF, FGF), whether or not they are mutated, or to the nuclear receptors of hormones (notably, androgens, estrogens, glucocorticoids).

The hormone receptors are frequently mutated in cancers and the invention pertains in this case to the use of oligonucleotides recognizing the mutated forms of these receptors, which do not inhibit the synthesis of the wild forms. This makes it possible, for example, in the case of prostate carcinomas that have become resistant by mutation of the androgen receptor, to treat patients via the systemic route with siRNAs that block the synthesis of the mutated receptor without inducing the castration effects linked to the inhibition of the wild forms of the receptor in other organs. In fact, the Applicants' present an example using oligonucleotides recognizing mutated forms of the receptor.

The cell cycle can also be stopped by inhibiting the synthesis of proteins indispensable for its unfolding such as, for example, cyclins, cyclin-dependent kinases, DNA-replication enzymes, transcription factors such as E2F.

Induction of necrosis results from the requirement of the tumor cells for oxygen and nutriments. A tumor initially provides for its development from the preexisting vessels of the host. Beyond 1 to 2 mm in diameter, the cells located at the center of the tumor are in hypoxia. This hypoxia, via the intermediary of a proline hydroxylase, leads to the stabilization of the transcription factor Hif1α, whose sequence, SEQ ID NO. 59, is presented in the attachment, which by attaching itself on the HRE sequences in the promoters of its target genes triggers the hypoxic reaction. This reaction leads to the activation of about a hundred genes enabling activation, notably of the pathway of anaerobic glycolysis, which is the stress response, and angiogenesis. This latter mechanism activates the VEGF gene, whose sequence, SEQ ID NO. 60, is presented in the attachment, which is the principal tumoral angiogenic factor.

Thus in one embodiment, the oligonucleotides according to the invention block, for example, the expression of the transcription factor Hif1α or, for example, that of VEGF making the tumor cells incapable of mounting a hypoxic or angiogenic response. Angiogenesis is a mechanism that is normally repressed in the adult with the exception of the menstrual cycle (uterus ovaries). The inhibition of this mechanism therefore has few consequences for normal tissues.

In one embodiment, the invention relates to an oligonucleotide of which one of said oligonucleotide sequences is substantially complementary to a target sequence belonging to a molecule of DNA or messenger RNA of the gene coding:

the transcription factor Hif1α;
one or more isoforms of VEGF A or a member of the family of this growth factor.

In certain cancers, the tumoral phenotype results from or is maintained by the expression of a protein normally absent from normal cells. This protein can result from the present or prior expression of a viral genome in the cell such as that of the papilloma virus (HPV) or the hepatitis B virus. This protein can also result from the mutation (punctiform, deletion, insertion) of a normal cellular gene. In this case, it is frequent that the mutated protein thereby produced possesses negative transdominant properties in relation to the normal protein. The specificity of the siRNA enables inhibition of the synthesis of the mutant protein without blocking the synthesis of the wild proteins. Two examples relating to the mutated form of the protein p53 and the androgen receptor are reported in the experimental section below.

The research studies performed in the framework of the invention demonstrate that these oligonucleotides are particularly suitable in one embodiement for repressing harmful genes implicated in canceration and more particularly those genes leading to the formation of fusion proteins in cancerous cells, such as the fusion protein PML-RAR alpha.

Thus in one embodiemnt, the invention relates to oligonucleotides whose sequence is complementary to a target sequence belonging to a gene resulting from a chromosomal translocation so as to inhibit the effects of the fusion protein expressed by this gene. Thus, the target sequence corresponds to the sequence of the junction of the fusion protein.

Table 2 of attachment A is a nonexhaustive list of the fusion proteins representing therapeutic or diagnostic targets for the oligonucleotides of the invention.

Targeting the junction between two genes with an oligonucleotide of the invention, for example, the two genes pml and rarα, makes it possible to attain specific inhibition of the fusion protein without affecting the biological role of the natural proteins which can be coded by the second allele. This form of implementation of the invention thus encompasses all of the fusion proteins implicated in carcinogenesis, particularly the leukemias. Further, the reciprocal forms as well as all of the variants of the fusion proteins cited in the attachment also constitute targets of the invention. In one embodiement, the invention thus relates to the use of oligonucleotides, as described above, for the preparation of a pharmaceutical composition intended for the treatment of diseases resulting from the expression of a fusion protein, and in particular for the treatment of cancers.

The present anticancer therapies target the cancerous cells, by different approaches that are employed in isolation or combined with each other (chemotherapy, surgery, radiotherapy, immunotherapy). The therapeutic failures are massively due to either the cells not having been reached by the treatment or, primarily, by cells that are mutated in response to the treatment. The capacity for mutation is greatly facilitated by the genetic instability of the tumor cells. The inhibition of tumor vascularization, depriving the cells of oxygen and nutriments, has in the past several years opened new therapeutic perspectives in cancer research. This strategy, which is complementary to the previously mentioned methods, targets the normal endothelial cell of the host, which is genetically stable and theoretically not likely to mutate. Numerous clinical trials directed at inhibiting tumoral angiogenesis via different approaches are underway worldwide. However, the initial reported results appear to be rather disappointing.

The inventors have demonstrated that tumors are capable of compensating for the effects of angiogenesis inhibitors by selecting subpopulations of cells secreting strong concentrations of pro angiogenic factors.

Tumors are not comprised of homogeneous cells with regard to their genetic expression. This is attested to by a very large number of studies in which immunolabeling was performed for a large variety of antigens in the tumors. Macroscopically, a tumor is frequently composed of regions that are highly vascularized alongside zones of necrosis or avascular regions.

This tumor heterogeneity promotes the ability of tumors to escape from the applied treatments, no matter what their nature. The greater the diversity of the genetic expression in a tumor, the greater the probability that there exists at least one cell capable of resisting an antitumor agent. It therefore appears to be essential to combine different strategies in order to first reduce the tumoral heterogeneity and avoid the escape phenomena.

In another embodiment, The invention relates to siRNAs that are inhibit the expression of genes responsible for the inactivation of p53 and their use in the treatment of cancers. p53 is the product of a tumor-suppressor gene or antioncogene, mutated in more than 50% of the tumors in humans. p53 is thus considered to be a guardian of the genome. It is activated in the cells in the case of genotoxic stress and participates in various processes including the induction of the programmed death process.

In 74% of the cases of monoallelic mutation, the inactivation of p53 is due to a punctiform mutation leading to the expression of protein that is mutated but of normal size. It is generally considered that the mutated version forms heteromers with the product of the wild allele on which it acts as a negative transdominant that blocks its activity. The mutant form also appears to have an oncogenic activity in itself. Thus, the mutated forms of p53 are capable of activating the gene MDR, which facilitates the resistance of the cancerous cells to chemotherapy. Moreover, the expression of mutants of p53 is associated with a stronger tumoral angiogenesis, probably because the mutant forms of p53 are no longer capable of stimulating the transcription of the gene of thrombospondin, one of the most powerful repressors of angiogenesis, and activate VEGF and bFGF, two powerful activators of angiogenesis. Moreover, the cells in which a mutated form of p53 is expressed lose various levels of regulation. In particular, they are no longer capable of initiating a programmed death process which constitutes one of the major protection processes against tumorigenesis. The restoration of wild type p53 activity in cultured tumor cells leads to the restoration of this cellular response. Thus, inhibiting the expression of the mutated forms of p53 represents a potentially powerful tool in anticancer therapy.

At present, there is no effective means for restoring p53 activity in human cancer cells. With regard to the cancers in which both alleles are inactivated, attempts to restore the p53 activity by gene therapy are envisaged. These approaches are complicated by the use of viral vectors that at present do not appear to be very effective.

Furthermore, it has been observed specifically in cervical cancers linked to infection by the HPV virus of the cells of the neck of the uterus that p53 can be inactivated by the overexpression of a viral protein. In fact, this virus codes for a protein, the protein E6, which inactivates p53. In this type of cancer, it is the inhibition of the protein E6 which could restore a wild p53 activity.

The invention has as one object providing new means enabling activation of p53 by inhibiting the expression of the genes responsible for its inactivation. The research studies performed in the framework of the present invention demonstrated that it was possible to repress in a very effective and very specific manner the expression of a mutant form of p53.

The invention pertains to oligonucleotides presenting a sequence complementary to a specific polynucleotide sequence of the gene of the mutated p53. Thus, these are oligonucleotides whose sequence bear a mutation in relation to the sequence of wild p53. The sequence of the wild gene of p53 is shown in the attached sequence listings as SEQ ID NO. 1. The different mutations that can intervene in the sequence of p53 are indicated in table 3 of attachment B at the end of the present description.

The mutations observed most frequently in cancerous pathologies are presented in table 4 below.

TABLE 4

| Position | Wild p53 | |
|----------|----------|---|
| R273H | GAGGTGCGTGTTTGTGC | SEQ ID NO. 61 |
| R248Q | gcaTgaaccggaggcccaT | SEQ ID NO. 62 |
| R248W | gcaTgaaccggaggcccaT | SEQ ID NO. 63 |
| R249S | gcaTgaaccggaggcccaT | SEQ ID NO. 64 |

TABLE 4-continued

| G245S | CTGCATGGGCGGCATGAAC | SEQ ID NO. 65 |
|---|---|---|
| R282W | TGGGAGAGACCGGCGCACA | SEQ ID NO. 66 |
| R175H | TGTGAGGCACTGCCCCCAC | SEQ ID NO. 67 |
| C242S | TAACAGTTCCTGCATGGGCG | SEQ ID NO. 68 |
| Position | Mutated p53 | |
| R273H | GAGGTGCATGTTTGTGC | SEQ ID NO. 69 |
| R248Q | gcaTgaacCAgaggcccaT | SEQ ID NO. 70 |
| R248W | GCATGAACTGGAGGC CAT | SEQ ID NO. 71 |
| R249S | gcaTgaaccggagTcccaT | SEQ ID NO. 72 |
| G245S | CTGCATGGGCAGAGCATGAAC | SEQ ID NO. 73 |
| R282W | TGGGAGAGACTGGCGCACA | SEQ ID NO. 74 |
| R175H | TGTGAGGCGCTGCCCCCAC | SEQ ID NO. 75 |
| C242S | TAACAGTTCCTCCATGGGCG | SEQ ID NO. 76 |

Thus, the oligonucleotides according to one aspect of the invention are complementary to a target sequence belonging to the mutated gene of p53 carrying at least one of the mutations presented in table 3, and most particularly at least one of the mutations of table 4 above.

These oligonucleotides are capable of discriminating in an effective manner between the wild form and the mutated form of p3. The strategy is to block the expression of the mutated form to reactivate the wild form and induce in the cells a programmed death process for which the wild form is indispensable and/or to block any other process induced by the wild form of p53. Moreover, this discrimination capacity of the oligonucleotides of the invention makes it possible to not touch the cancerous cells and to spare the normal cells, which do not express this mutated form of p53.

Reference will be made in the examples to the figures in which:

FIG. 1A is a schematic representation of the proteins RARα, PML and the associated fusion protein, PML-RARα. FIG. 1B represents the results of transfections with an siRNA directed against PML-RARα.

Figure 2:
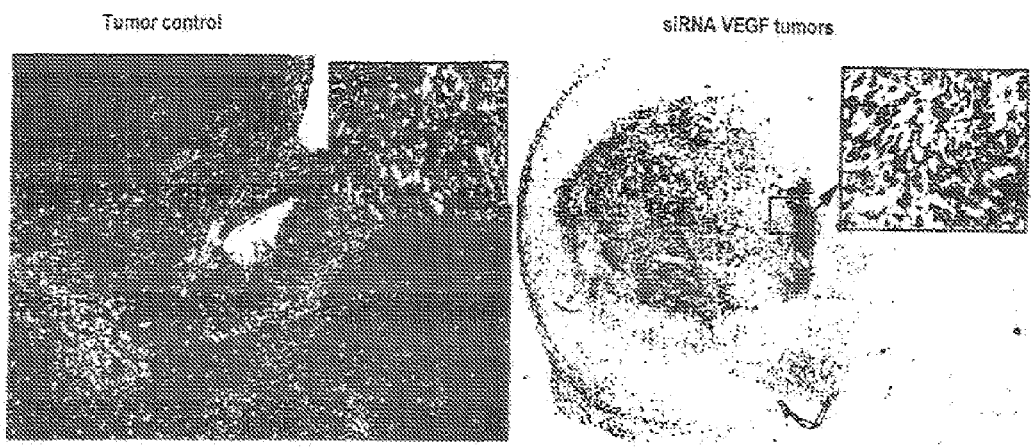
FIG. 2 pertains to the inhibition of the expression of VEGF by siRNA directed against this protein and the consequences of this inhibition.

FIG. 2 pertains to the inhibition of the expression of VEGF by siRNA directed against this protein and the consequences of this inhibition. FIG. 2A represents the immunodetection of VEGF in the cJ4 or LNCaP cells transfected by the control siRNA or a siRNA directed against VEGF. FIG. 2B represents the quantification using ELISA of VEGF in conditioned medium of cj4 cells transfected by the control siRNA or the siRNA VEGF as a function of time after transfection. FIG. 2C represents the growth curve in nude mice of tumors stemming from the subcutaneous injection of $10^6$ cells of cJ4 that is not transfected, transfected by the control siRNA or the siRNA VEGF. FIG. 2D represents the appearance of the tumors on day 7 after injection of the cells. FIG. 2E represents the immunodetection of VEGF in tumors stemming from the injection of cJ4 cells transfected with the control siRNA or the siRNA VEGF after 12 days of development in vivo.

Figure 3:
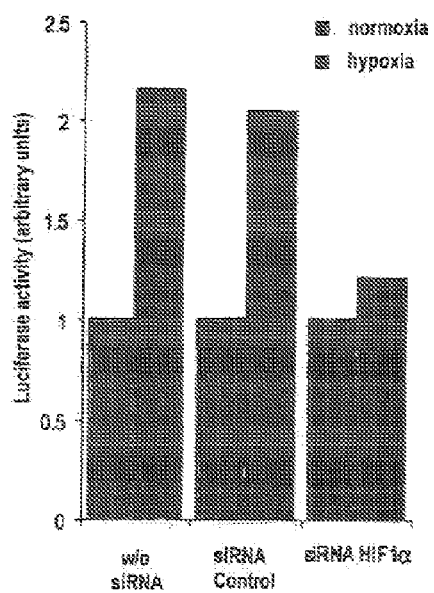
FIG. 3 shows the effect of inhibition by a siRNA specific of the expression of a transcription factor, HIF1α, on the transcriptional response to hypoxia. It also shows the measurement of the activity of a reporter VEGF luciferase in response to hypoxia in CJ4 cells that are not transfected, by the control siRNA or by the siRNA directed against HIF1α.

FIG. 3 pertains to the effect of inhibition by a siRNA specific of the expression of a transcription factor, HIF1α, on the transcriptional response to hypoxia. The figure represents the measurement of the activity of a reporter VEGF luciferase in response to hypoxia in CJ4 cells that are not transfected, transfected by the control siRNA or by the siRNA directed against HIF1α.

Figure 4:
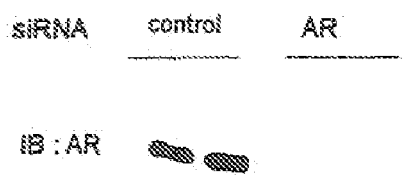
FIG. 4 shows the inhibition by siRNA specific of the expression of the androgen receptor in the cells and functional consequences of these inhibitions.
Figure 4:
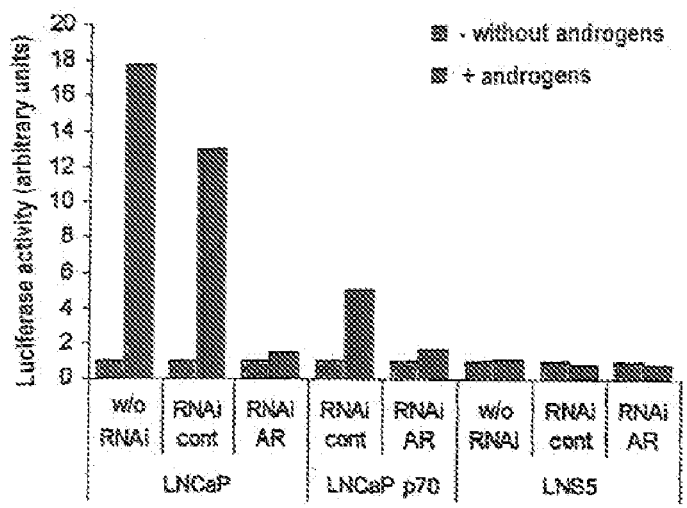
Figure 4:
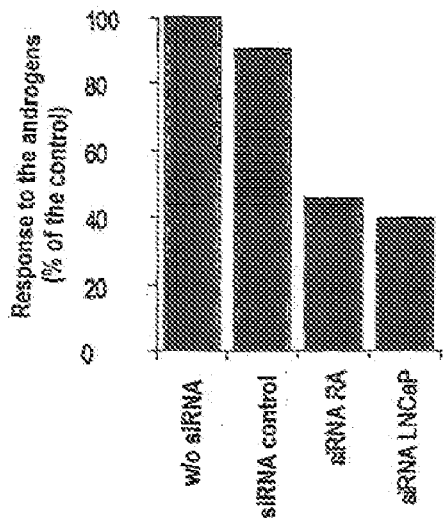
Figure 4:
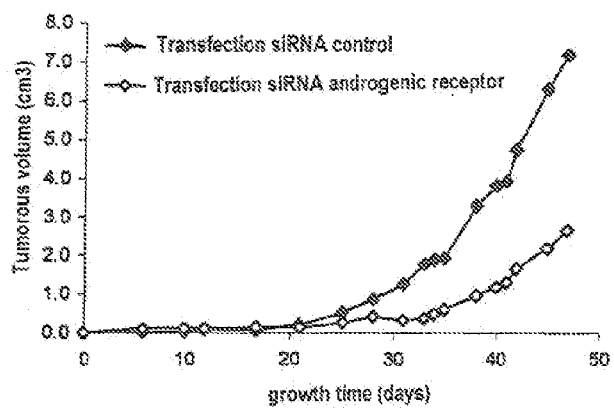
Figure 4:
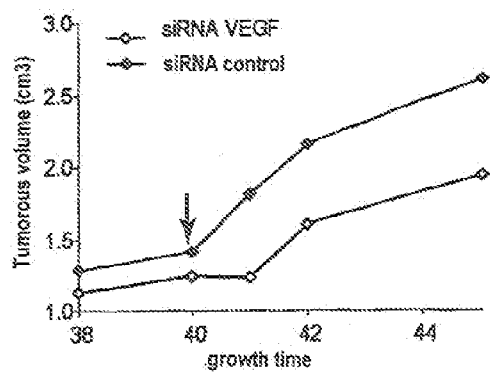
Figure 4:
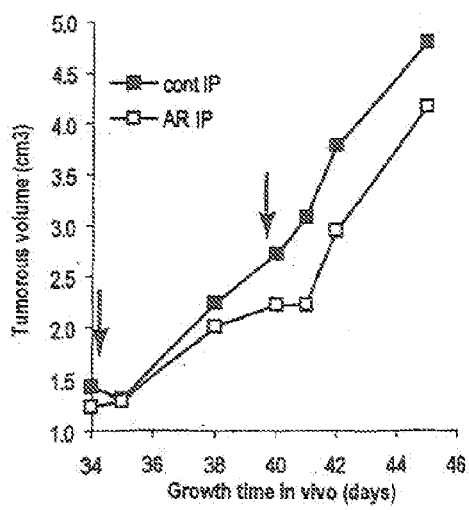

FIG. 4 pertains to the inhibition by siRNA specific of the expression of the androgen receptor in the cells and functional consequences of these inhibitions. FIG. 4A represents the detection by immunoblot of the expression of the androgen receptor 48 h after transfection of the LNCaP cells by a control siRNA or a siRNA directed against the androgen receptor (AR). FIG. 4B represents the measurement of the activity of a reporter 4×ARE luciferase to R1881 in various clones of the line LNCaP not transfected, or transfected by control siRNA or by siRNA AR. FIG. 4C represents the comparison of the response to R1881 of LNCaP cells that were not transfected (100%), and LNCaP cells transfected by a control siRNA, a siRNA directed against the androgen receptor (AR) or a siRNA recognizing specifically a punctiform mutation present in the androgen receptor of the line LNCaP. FIG. 4D represents the growth in nude mice of tumors resulting from the subcutaneous injection of LNCaP cells transfected by a control siRNA or by a siRNA directed against the androgen receptor. FIG. 4E represents the growth of LNCaP tumors in mice having received on the $40^{th}$ day after implantation of the cells an intravenous injection in the tail vein of 2 µg of siRNA directed against VEGF or of control siRNA. FIG. 4F represents the growth of LNCaP tumors in mice having received on the $34^{th}$ and $40^{th}$ days after implantation of the tumor cells an intraperitoneal injection of 2 µg of siRNA directed against the androgen receptor or control siRNA.

Figure 5:
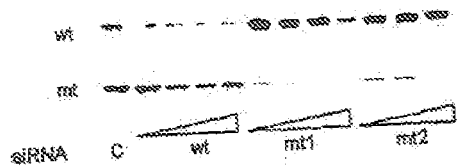
FIG. 5 shows the inhibition of the expression of wild or mutant forms of p53 by siRNAs and the functional consequences of these inhibitions.
Figure 5:
Figure 5:
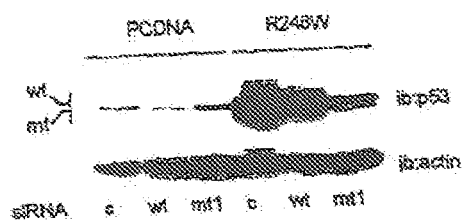
Figure 5:
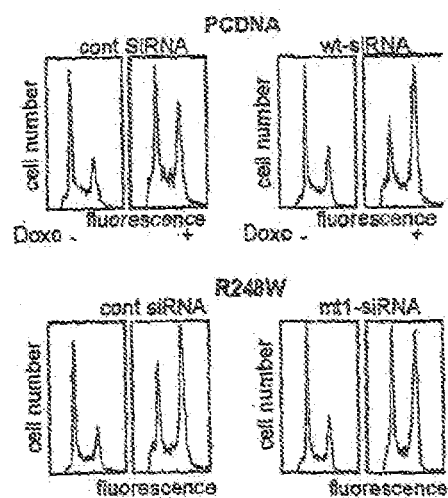

FIG. 5 pertains to the inhibition of the expression of wild or mutant forms of p53 by siRNAs and the functional consequences of these inhibitions. FIG. 5A represents the sequence of human p53 protein, which is further disclosed in sequence listing as SEQ ID NO:1. FIG. 5B represents the specific, dose-dependent inhibition by the siRNAs of the expression of wild or mutant forms of p53 transfected in cells not initially expressing it. FIG. 5C represents the specific inhibition by siRNAs of the simultaneous or not simultaneous expression of wild or mutant forms of p53 transfected in cells not initially expressing it. FIG. 5D represents the inhibition of the expression of wild endogenous p53 or a mutant form of 53 transfected by siRNA. FIG. 5E represents the effect of the inhibition of p53 by siRNAs on the resistance to genotoxic stress. FIGS. 5 F, G, H and I represent the inhibition of the expression of a mutant form of p53 in the cells of a patient with Li-Fraumeni cancer syndrome at the level of the mRNA (5G) and the expression of the protein by immunoblot (GF) or in indirect immunofluorescence (5H) and the consequences on the resistance of these cells to genotoxic stress. FIG. 5J shows the inhibition by the siRNAs specific of the dependent transfection of the wild or mutant forms of p53. FIG. 5K shows the inhibition of the expression of one of the target genes of p53, p21, inhibitory protein of cellular proliferation, by the coexpression of mutant forms of p53 and the restoration of this expression by treatment of the cells with a siRNA inhibiting the synthesis of the mutant form of p53.

Figure 6:
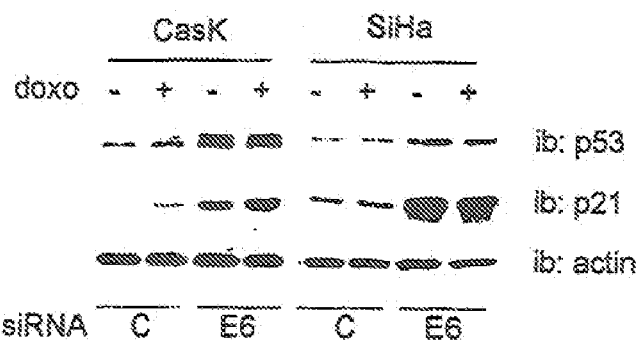
FIG. 6 shows the inhibition of the expression of the protein E6 of the human papilloma virus HPV by specific siRNAs and the consequences of this inhibition.
Figure 6:
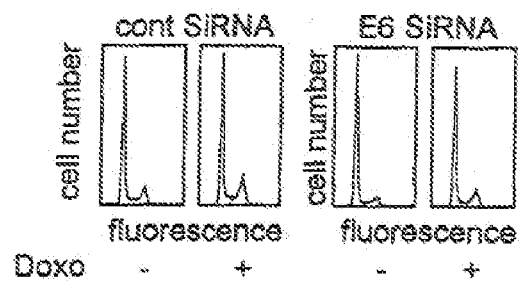
Figure 6:

FIG. 6 pertains to the inhibition of the expression of the protein E6 of the human papilloma virus HPV by specific siRNAs and the consequences of this inhibition. FIG. 6A represents the sequence of the HPV protein, which is further disclosed in sequence listing as SEQ ID NO:2. FIG. 6B represents the effect of inhibition by siRNAs specific of the expression of protein E6 of HPV in cells that express this virus, on the expression of p53 and p21. FIGS. 6C and 6D represent the effect of the inhibition of the expression of the protein E6 of HPV on the cell cycle.

Figure 7:
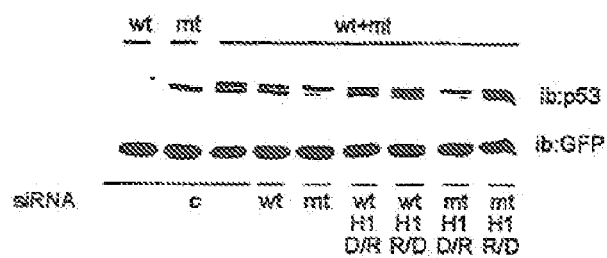
FIG. 7 shows the use of hybrid siRNAs comprising DNA bases and RNA bases.
Figure 7:
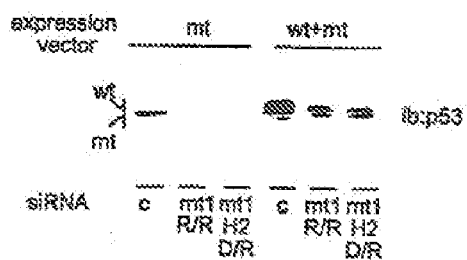

FIG. 7 pertains to the use of hybrid siRNAs comprising DNA bases and RNA bases. FIGS. 7A and 7B represent the effect of siRNAs DNA/RNA hybrids on the expression of the GFP expression by transfection of the cells. FIG. 7C compares the effect of RNA/RNA, DNA/RNA and RNA/DNA siRNAs at constant dose on the inhibition of the transcription induced by the androgen receptor. FIGS. 7D and 7E represent the effects of a substitution of RNA bases by DNA bases in the siRNA sequence inhibiting the synthesis of p53.

Figure 8:
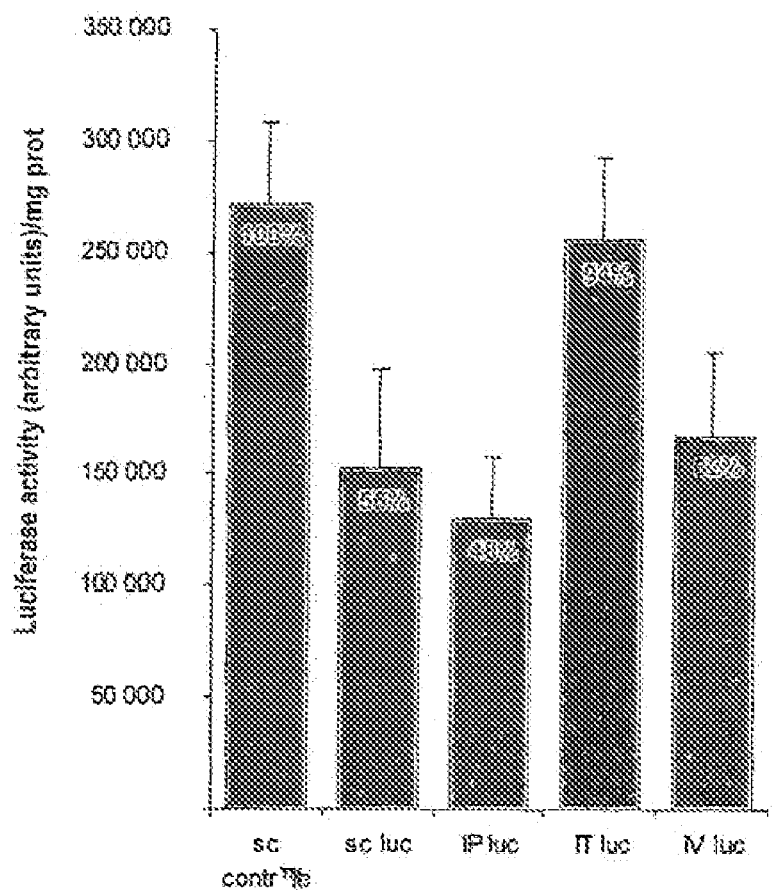
FIG. 8 shows the inhibition of luciferase in tumors expressing this enzyme by injection of siRNA via the subcutaneous, intratumoral, intraperitoneal or intravenous route.

FIG. 8 pertains to the inhibition of luciferase in tumors expressing this enzyme by injection of siRNA via the subcutaneous, intratumoral, intraperitoneal or intravenous route.

p53 can be inactivated via many distinct mechanisms. For example, in the majority of cervical cancers p53 is inactivated by E6, a protein coded by the human papilloma virus. E6 leads to the ubiquitinylation of p53 which leads to its degradation by the proteasome. In this case, the expression of p53 can be restored by inhibition of the expression of the protein E6. The aspects of this invention also relates to oligonucleotides presenting a sequence complementary to a specific polynucleotide sequence of the gene of the protein E6 of HPV. The sequence of the gene of the protein E6 of HPV is given in FIG. 6A as well as in the attached sequence listings as SEQ ID NO. 2.

As previously indicated, a strategy according to the invention has as its goal to block using RNAi the expression of the androgen receptor in carcinomas. The sequence of the androgen receptor is given in the attached sequence listings as SEQ ID NO. 77. In order to treat carcinomas before they became resistant or to treat those that had become resistant by amplification of the receptor without mutation, siRNA homologous to a region for which no mutation had been described in the data banks of mutations of the androgen receptors (indicated as siRNA AR) were used. In order to treat specifically the prostate carcinomas that had become androgen resistant by mutation, a sequencing of the mRNA coding for the receptor was performed in the patient's cells in order to devise a specific sequence of the mutation, making it possible to treat the patient without consequence for the normal cells. An example is presented for the use of siRNA recognizing specifically the mutation of the androgen receptor present in the cell line LNCaP (siRNA LNCaP). Consequently one aspect of the invention relates to oligonucleotides substantially complementary to a target sequence belonging to a DNA or messenger RNA molecule coding the mutated or nonmutated androgen receptor. For example, the androgen receptor bearing at least one of the mutations presented in table 5 of attachment C. These oligonucleotides of the invention are specific to the androgen receptor and are useful for treating or preventing androgen-dependent diseases, such as, e.g., prostate cancer.

Other advantages and characteristics of the invention will become apparent from the examples below pertaining to:

Example 1: Inhibition of the protein PML-RARα associated with acute promyelocytic leukemia (APL).
Example 2: Inhibition of the tumoral angiogenesis induced by VEGF.
Example 3: Inhibition of the hypoxic response induced by HIF1α.
Example 4: Inhibition of the wild or mutant forms of the androgen receptors in prostate carcinoma cells.
Example 5: Inhibition of the wild or mutant forms of the protein p53.
Example 6: Inhibition of the viral protein E6.
Example 7: Use of DNA/RNA hybrids to inhibit the expression of various proteins.
Example 8: In vivo administration of siRNA via different routes.

EXAMPLE 1

Inhibition of the Protein PML-RARα Associated with Acute Promyelocytic Leukemia (APL)

I—Introduction

Acute promyelocytic leukemia (APL) is due to the translocation t(15 ;17) on chromosome 15. In patients afflicted with APL, the receptor of retinoic acid (RARα) is fused to the protein PML (promyelocytic leukemia protein) thereby generating the fusion protein PML-RARα. Five fusion proteins bringing RARα into play have been identified to date. All of these leukemia types implicate the RARα receptor and are clinically similar, which suggests that the rupture of the transduction pathway of retinoic acid is crucial in the pathogenesis of APL leukemia.

The fusion protein PML-RARα retained the binding domains of the DNA and retinoic acid of the RARα. It has been shown that the fusion protein PML-RARα represses the expression of the target genes of retinoic acid and thereby also blocks the differentiation of the promyelocytic cells. Only the administration of pharmacological doses of retinoic acid remove transcriptional repression exerted by PML-RARα and restore cellular differentiation. Moreover, the protein portion PML of the fusion protein could also intervene in the mechanism of the blocking of the transduction pathway by retinoic acid. To the extent that PML functions as a growth inhibitor and an apoptotic agent and that it is required for the expression of certain genes induced by retinoic acid, the dominant negative effect of PML-RARα on PML could allow cells to acquire a growth capacity, a resistance to apoptosis and a termination of differentiation.

Cellular biology studies of PML have shown that this protein possesses a particular localization in the nucleus, in structures called nuclear bodies. It appears that these structures are in direct relation with the anti-oncogene role of PML. In malignant APL cells, the protein PML-RARα induces, by heterodimerization with PML, the delocalization of PML from the nuclear bodies to the micropunctuated structures that could correspond to PML-RARα anchorage sites on the chromatin. This delocalization could block the pro-apoptotic function of PML and its role in myeloid differentiation. Multiple research teams have shown that combined treatment with retinoic acid and $AS_2O_3$ on cell lines that express the fusion protein PML-RARα enable the degradation of the fusion proteins at the same time as a relocalization of PML on the nuclear bodies. This reorganization of the nuclear bodies restores the functions of PML and contributes to the restoration of differentiation.

Finally, the chimera protein PML-RARα would thus have a double dominant negative effect on RARα and on PML enabling the cells to escape from apoptosis and blocking the differentiation of the thereby transformed promyelocytes.

More than 98% of the patients suffering from APL leukemia present the translocation t(15 ;17) (q22 ;q21) which leads to the formation of fused genes PML-RARα and RARα-PML. There exist two subtypes of fusion proteins PML-RARα: the S (short) fusions and the L (long) fusions). The long form of the fusion protein PML-RARα corresponding to a protein of 955 amino acids representing the predominantly expressed form, and thus was taken as model in this study (Attachments A, B and C). This protein comprises amino acids 1 to 552 of the protein PML fused with amino acids 59 to 462 of the α receptor of retinoic acid (RARα).

II—Preparation and Administration of the Oligonucleotides

Complementary RNA oligonucleotides corresponding to the sequence of the junction of the gene of the fusion protein, i.e., 10 nucleotides of the PML gene and 10 nucleotides of the RARα gene, were synthesized with addition of two deoxythymidines at 3' (FIG. 1). These oligonucleotides were hybridized and the production of the double-strand oligonucleotide was verified on acrylamide gel.

The sequences of the PML-RAR and control siRNAs used (5'-3') are presented below.

Control:

```
FW:
[CAUGUCAUGUGUCACAUCUC]RNA[TT]DNA      (SEQ ID NO.3)

REV:
[GAGAUGUGACACAUGACAUG]RNA[TT]DNA      (SEQ ID NO.4)

PR:

Sense:
[GGGGAGGCAGCCAUUGAGAC]RNA[TT]DNA      (SEQ ID NO.5)

Antisense:
[GUCUCAAUGGCUGCCUCCCC]RNA[TT]DNA      (SEQ ID NO.6)
```

III—Results

NIH3T3 fibroblasts were cotransfected with lipofectamine by an expression vector of the protein PML-RARα (100 ng) and by 500 ng of control siRNA (C) or siRNA directed against PML-RARα (PR). 48 h after transfection, a Western blot (FIG. 1B) was performed on the total cell extracts using an antibody which recognized the protein RARα, whole or in fusion protein form.

FIG. 1B shows that the transfection of siRNA PR very strongly inhibits the expression of fusion protein PML-RARα compared to the cells transfected with the control siRNA (C) without modifying the expression of the protein RARα.

EXAMPLE 2

Inhibition of Tumoral Angiogenesis by VEGF

I—Introduction

VEGF (vascular endothelial growth factor) is one of the most powerful angiogenic factors identified. These factors are overexpressed in numerous situations of pathological hypervascularization and notably in tumoral development. The inhibition of this angiogenesis enables blocking of tumor growth. The method has the goal of inhibiting tumoral angiogenesis by blocking the expression of one of these angiogenic factors, and as seen in this example, that of VEGF by the tumor cells.

II—Preparation and Administration of the Oligonucleotides

Two RNA oligonucleotides, complementary of a region of the coding sequence of human VEGF, conserved in the rat and the mice, were synthesized. Two deoxynucleotides (TT) were added at 3':

Sequence of the RNAi VEGF:

```
                                    (SEQ ID NO.7)
5'[AUGUGAAUGCAGACCAAAGAA]RNA-TT[DNA]

(SEQ ID NO.8)
5'[UUCUUUGGUCUGCAUUCACAU]RNA-TT[DNA]
```

Sequence of the control RNAi:

```
                                    (SEQ ID NO.9)
5'[CAUGUCAUGUGUCACAUCUC]RNA-TT[DNA]

(SEQ ID NO. 10)
5'[GAGAUGUGACACAUGACAUg]RNA-TT[DNA]
```

These oligonucleotides or the control oligonucleotides, whose sequence presents no homology with the sequences stored in the data banks, were hybridized and transfected using the Polyfect kit (Qiagen) in the cells of a rat fibrosarcoma (cJ4) and in human cells of the prostate carcinoma LNCaP.

III—Results 48 h after transfection, an indirect immunofluorescence was performed to detect the expression of the protein in the cells. FIG. 2A shows a massive inhibition of the expression of VEGF.

In order to quantify this effect, quantitative determination of the VEGF in the transfected CJ4 cells in parallel with the control RNAi or with the RNAi VEGF was performed with ELISA (quantikine, R&D). The cells were incubated for 48 h prior to the quantitative determination in a medium containing 1% serum. The determination was performed 4 days and 6 days after transfection. Under these conditions, FIG. 2B shows an inhibition of the secretion of VEGF of 85% at 4 days and of 75% at 6 days and of 60% at 13 days in the cells transfected with the RNAi VEGF compared to the cells transfected with the control RNAi (FIG. 2B).

The effect of the inhibition of VEGF on the tumor cells was tested in vivo: 3 days after transfection, three groups of 4 female nude mice aged 4 weeks were injected subcutaneously at the rate of one million cells per mouse: the first group was injected with nontransfected cells, the second group was injected with cells transfected by the control RNAi, the third group was injected with cells transfected with RNAi VEGF. No selection of the transfected cells was performed before the injection.

Tumor growth was monitored by measuring the volume of the tumors at regular intervals (FIG. 2C).

FIGS. 2C and 2D do not show any significant difference between the sizes of the tumors in groups A and B. A very large reduction in the tumor volume was seen in group C. The appearance of the tumors, much whiter in group C (FIG. 2D), manifested a pronounced decrease in the tumoral vascularization. After sacrifice of the animals on day 12 after the injection, the tumors were dissected, fixed and immunodetection of VEGF was performed on sections of these tumors. There was seen a very strong reduction in the expression of VEGF in the tumors of group C compared to that of group B (FIG. 2E).

In another experiment, tumors were induced in male nude mice by injection of prostate carcinoma cells LNCaP. 40 days after injection, the volume of the tumors having reached 1 to 1.5 cm$^3$, the mice were divided into two groups. The first group (4 mice) received an intravenous injection in the tail vein of 2 micrograms of control siRNA in 100 µl of PBS. The second group received an equivalent dose of siRNA VEGF under the same conditions. It was observed that the siRNA VEGF but not the control siRNA induced a transitory suspension in tumor growth (FIG. 4D).

EXAMPLE 3

Inhibition of the Hypoxic Reaction

I—Introduction

Certain tumors are capable of developing under strongly anoxic conditions. This is seen very frequently in tumors of regions that are very poorly vascularized. This weak sensitivity to hypoxia has two consequences: on the one hand, an antiangiogenic treatment has little chance of being effective on these tumors or these tumor subpopulations. On the other end, this weak vascularization makes it difficult to deliver the therapeutic molecules. The transcription factor Hif1α regulates the activity of more than 100 genes enabling the hypoxic response. The inhibition of this transcription factor in hypoxic tumors has the goal of blocking their growth.

II—Preparation of the Oligonucleotides
RNAi Hif1α

(SEQ ID NO. 11)
5' [CAUGUGACCAUGAGGAAAUGA] RNA-TT [DNA]

(SEQ ID NO. 12)
5' [UCAUUUCCUCAUGGUCACAUG] RNA-TT [DNA]

Control RNAi (SEQ ID NO. 13)
5' [GAUAGCAAUGACGAAUGCGUA] RNA-TT [DNA]

(SEQ ID NO. 14)
5' [UACGCAUUCGUCAUUGCUAUC] RNA-TT [DNA]

III—Results

The VEGF promoter contains a response element to the transcription factor Hif1α. In order to test in vitro the effect of an RNAi directed against Hif1α, we transfected cJ4 cells with a reporter vector VEGF-luciferase, alone or in combination with an RNAi Hif1α or control.

24 h after transfection, the cells were incubated for 18 h in medium without serum, with the addition in some cases of cobalt chloride 100 µM in order to produce hypoxic conditions; the luciferase activity was then measured.

FIG. 3 shows that a complete inhibition of the induction of the response of the promoter VEGF to hypoxia was observed when the cells were transfected with RNAi Hif1α but not with the control RNAi.

EXAMPLE 4

Inhibition of the Wild or Mutant Forms of the Androgen Receptors in Prostate Carcinomas I—Introduction The prostate carcinomas are the second cause of cancer mortality for men in the industrialized countries. They are the cause of more than 9500 deaths per year in France. The prostatic epithelial cells are dependent on androgens for their growth. Prostatic carcinomas are initially androgen dependent. Chemical castration thus initially can block the growth of the carcinoma. However, in all cases, these carcinomas become androgen independent and their prognosis becomes very negative. This androgen independence—depending on the individuals—is often due to a mutation of the receptor (conferring on it, for example, a response to estrogens or to glucocorticoids) or to an amplification of the receptor.

II—Preparation of the Oligonucleotides

Two RNA oligonucleotides complementary to a region of the coding sequence of the nonmutated human androgen receptor (AR) were synthesized. Two deoxynucleotides (TT) were added at 3'. In other experiments, siRNAs named LNCaP and specifically recognizing the mutation of the androgen receptor (T877A) in the cells of human prostate carcinoma LNCaP, were used.

AR:

(SEQ ID NO. 15)
5' [GACUCAGCUGCCCCAUCCACG] RNA-TT [DNA]

(SEQ ID NO. 16)
5' [CGUGGAUGGGGCAGCUGAGUC] RNA-TT [DNA]

Control:

(SEQ ID NO. 17)
5' [GAUAGCAAUGACGAAUGCGUA] RNA-TT [DNA]

(SEQ ID NO. 18)
5' [UACGCAUUCGUCAUUGCUAUC] RNA-TT [DNA]

LNCap:

(SEQ ID NO. 19)
5' [GCAUCAGUUCGCUUUUGAC] RNA-TT [DNA]

(SEQ ID NO. 20)
5' [GUCAAAAGCGAACUGAUGC] RNA-TT [DNA]

Multiple subclones of the human prostate carcinoma line LNCaP were used in this study. The original line, LNCaP, is androgen dependent. The cells LN70, obtained by repeated passages of the line LNCaP in vitro have a diminution in their response to androgens. The clone LNS5, obtained after passage of the animals in an animal, is androgen resistant.

III—Results

The LNCaP cells were transfected in vitro with siRNA AR or control siRNAs using the transfection agent Polyfect (Qiagen). 48 h after transfection, the cells were detached from their support. Half of the cells were used for performing a Western blot detection of the androgen receptor; the other half were put back in culture. The androgen receptor (band at 110 kDa) was no longer detectable by Western blot in the cells transfected by siRNA AR (FIG. 4A). The cells transfected by siRNA and put back in culture were found to be incapable of continuing their growth, to the opposite of the cells transfected by the control siRNA.

The level of response to the androgens was measured by transfecting different cellular clones of the lone LNCaP with a reporter vector placing the coding sequence of luciferase downstream of a minimal promoter flanked by 4 repetitions of the androgen response element (4×ARE). After transfection, the cells were incubated for 18 h in the absence of serum and in the presence or absence of a metabolically stable analogue of dihydrotesterone, R1881 (NEN). The ratio of the luciferase activities under these two conditions makes it possible to measure the level of response to the androgens of the reporter vector.

We measured the effect of the cotransfection in the control RNAi or RNAi AR cells on the response to the androgens of the different clones of the line LNCaP.

FIG. 4B shows a complete inhibition of the response to the androgens in the two androgen-sensitive clones: LNCaP and LNCaP p70. This method does not permit measurement of the response of the androgen-resistant clone LNS5 to the treatment by RNAi AR.

The androgen receptor present in the line LNCAP carries a mutation. We used two different siRNAs to inhibit its synthesis, the previously used siRNA AR and siRNA LNCaP specifically recognizing the mutation LNCaP. The response to the androgens was measured as in experiment 4B (FIG. 4C).

In order to study the effect of the inhibition of the expression of the androgen receptor on tumor growth in vivo of the prostate carcinoma cells, carcinoma cells LNCaP, transfected by a control siRNA (group A) or siRNA AR (group B) were injected subcutaneously in male nude mice. Tumor growth was monitored at regular intervals. It was seen that the tumors of the group B animals started growing later than those of group A and that the volume of the tumors of group B on the 48$^{th}$ day was markedly smaller than that of the tumors of group A (FIG. 4D).

In another experiment, LNCaP cells were injected in male nude mice. When, on the 34$^{th}$ day, the tumors had reached a volume comprised between 1.2 and 1.5 cm$^3$, the mice received via the intraperitoneal route an injection of 2 µg of control siRNA or siRNA AR in 100 µl of PBS. This injection was repeated on the 40 day. It was seen that the administration of siRNA AR leads to a slowing down of the tumor growth (FIG. 4F).

EXAMPLE 5

Inhibition of the Wild or Mutant Forms of the Protein p53

I—Preparation of the Oligonucleotides

The three siRNAs whose sequences are presented below were prepared, one directed against the wild form of p3 and the other directed against the mutated form expressed in a patient which resulted in the establishment of a line.

This mutation corresponds to one of the three observed most frequently in human tumors.

```
- wild p53:
                                          (SEQ ID NO. 21)
Sense: [GCAUGAACCGGAGGCCCAU]RNA[TT]DNA (SEQ ID NO. 22)
Anti:  [AUGGGCCUCCGGUUCAUGC]RNA[TT]DNA

- p53 MT1 (r248w):
                                          (SEQ ID NO. 23)
Sense: [GCAUGAACUGGAGGCCCAU]RNA[TT]DNA (SEQ ID NO. 24)
Anti:  [AUGGGCCUCCAGUUCAUGC]RNA[TT]DNA p53 MT2 (r248w):
                                          (SEQ ID NO. 25)
Sense: [UCAUGAACUGGAGGCCCAU]RNA[TT]DNA (SEQ ID NO. 26)
Anti:  [AUGGGCCUCCAGUUCAUGA]RNA[TT]DNA
```

The underlined nucleotides in the wild p53 are those that mutated in the mutant form and which are in italics in the sequences of the mutated form of mutated p53 (p53 MT1 and MT2). The bases in bold above are mutations which were introduced in order to augment the specificity.

II—Results

As shown in FIG. 5B, the H1299-NCI cells, which do not express p53, were transfected (using lipofectamine) by expression vectors (400 ng) of wild p53 (WT) or mutated p53 (MT). siRNAs (in increasing doses: 0, 125 ng, 250 ng, 500 ng and 1000 ng) directed against the wild form (WT), the mutated form (MT1 and MT2) or an irrelevant siRNA (C) were transfected at the same time. The cells were collected 24 hours later and analyzed by Western blot with an antibody directed against p53.

As shown in FIG. 5C, the H1299-NCI cells, which did not express p53, were transfected (using lipofectamine) by expression vectors (400 ng) of wild p53 (WT), mutated p53 (MT) or a mixture of the two (WT+MT) as indicated. siRNAs (400 ng) directed against the wild form (WT), the mutated form (MT1) or an irrelevant siRNA (C) were transfected at the same time. The cells were collected 24 hours later and analyzed by Western blot (ib: immunoblot) with cellular actin (Sigma) to monitor the amount of proteins used in the test.

As shown in FIG. 5D, U2OS cells (human osteosarcoma expressing a wild form of p53) were transfected in a stable manner either by a vector expressing a mutant form of p53 (R248W) or by the corresponding empty vector (pCDNA3). These lines were transfected by the indicated siRNAs and the expression of the indicated proteins was detected by Western blot.

In all cases, the siRNA directed against the mutated form of the protein inhibited the mutated form and the siRNA directed against the wild form inhibited the wild form. Furthermore, there was no crossed reaction because the siRNA directed against the wild form had no effect on the mutated form and vice versa. It should be noted that the expression of the mutant stabilizes the wild protein when it is co-expressed. Consequently, the inhibition of the mutant through its indirect effect brings the wild form to its base level without there being any inhibition of the expression of the protein.

As shown in FIG. 5E, the cells used in FIG. 5D were transfected by the indicated siRNAs. The cells were then subjected to a genotoxic stress by treatment with doxorubicin (200 ng/ml) for 24 h. FIG. 5E shows the analysis of the cell cycle of these cells by incorporation of propidium iodine and FACS analysis. The cells not transfected with the mutant form and thus only expressing the wild form (PCDNA cells) exhibited a high percentage of stopping at G1 in the presence of doxorubicin. The treatment of these cells with wild siRNA, diminishing the wild p53, reduced this stopping at G1. The cells expressing the mutated and wild form (R248W) stopped very little at G1 in the presence of doxorubicin, showing that the mutated form inhibits the activity of the wild form. When these cells were treated with siRNA MT1, they recovered a normal capacity (to compare with the untreated PCDNA controls) of stopping at G1, showing the restoration of the wild p53 activity in these cells.

As shown in FIGS. 5 F, G and H, the MDA 087 cells (stemming from a patient suffering from a Li-Fraumeni cancer syndrome and expressing the mutant R248W) were transfected with a siRNA directed against the mutant form (MT1) of p53, or with an irrelevant siRNA (C) (1.6 µg). Expression of p53 was detected in these cells by Western blot (FIG. 5F); the messenger RNAs were measured by quantitative CR (Light Cycler, Roche) (FIG. 5G) or immunofluorescence (FIG. 5H).

The MDA 087 cells were transfected with a siRNA recognizing the wild form (WT) or the mutated form (MT1) of p53 or by a control siRNA then subjected to a genotoxic stress by treatment with doxorubicin (200 ng/ml) for 24 h. The expression of the mutant form of p53 was detected by Western blot in the cells. It can be seen that the cells having received siRNA MT1 were not capable of stabilizing p53 in response to doxorubicin (FIG. 5I).

FIG. 5J shows the effect of the siRNAs MT1 and MT2 in cells that express the wild and mutated forms of p53. H1299-NCI cells, which do not express p53, were transfected (using lipofectamine) by a reporter vector carrying the gene of luciferase under control of a p53 response element and vectors of expression (400 ng) of the wild p53 (WT), mutated p53 (MT) or a mixture of the two (WT+MT), as indicated. siRNAs (400 ng) directed against the wild form (WT), the mutated form (MT1, MT2) or an irrelevant siRNA (C) were transfected at the same time. The cells were collected 24 hours later and analyzed for the expression of luciferase. Only the wild p53 activated the report vector and the co-expression of the mutant form inhibited this activity. The cotransfection of wild siRNA inhibited the expression of the wild protein and thus the residual activation of the reporter gene. The cotransfection of the siRNA MT1 and MT2, in contrast, restored this activation by blocking selectively the expression of the mutated form and preventing the negative transdominant effect that it exerts on the wild form of p53.

FIG. 5K shows a similar result on the expression of one of the targets of p53, the inhibitory protein of cell proliferation p21, in cells treated as in FIG. 5F. The expression of p21, detected by Western blot, was activated by wild p53 and inhibited when the mutant was co-expressed. This inhibition was lifted in the presence of siRNA MT1.

EXAMPLE 6

Inhibition of the Viral Protein E6

I—Preparation of the Oligonucleotides

A siRNA directed against the HPV protein E6 was also prepared. It responds to the following sequence:

```
    HPV-16-52
                                    (SEQ ID NO. 27)
Sense:  5' [CCACAGUUAUGCACAUAUC]RNA[TT]DNA (SEQ ID NO. 28)
Anti:   5' [GCUCUGUGCAUAACUUGG]RNA[TT]DNA.
```

II—Results

As shown in FIG. 6B, CasKi and SiHA cells, both expressing HPV protein E6, were transfected with the indicated siRNAs, treated or not treated as indicated with doxorubicin and analyzed by Western blot using the indicated antibodies. Treatment of the cells with siRNA E6 induced an augmentation in the expression of P53. This expression of p53 was manifested by an augmentation of the expression of the protein p21.

As shown in FIG. 6C, the cell cycle of the treated siHA cells as in FIG. 6B was analyzed by FACS. The figure represents a characteristic experiment. There was seen an augmentation of cells in phase G1 (FIG. 6D) in the cells treated with siRNA E6, an augmentation which was also seen in the cells when they were treated with doxorubicin.

EXAMPLE 7

Effect of the RNA/RNA Oligonucleotides and the DNA/RNA Hybrids

I—Introduction

The invention envisages the use of DNA/RNA hybrid oligonucleotides as alternative to the RNA/RNA oligonucleotides for inhibiting specifically the expression of a gene. In the case of the DNA/RNA hybrids, the sense strand is preferentially of a DNA nature and the antisense strand of a RNA nature. The other aspects related notably to the size of the oligonucleotides, the nature of the 3' ends and the mode of synthesis are the same as for the RNA/RNA oligonucleotides. The applications of these DNA/RNA hybrids are identical to those previously described for the RNA/RNA siRNA especially with regard to the therapeutic and diagnostic applications and the validation of genes. However, the doses of oligonucleotides employed in order to obtain the same effects with the DNA/RNA hybrids and RNA/RNA can be different.

II—Preparation of the Oligonucleotides

The sense strand is the one whose sequence is identical to that of the messenger RNA. The antisense strand is the strand complementary to the sense strand. By convention, in a duplex the nature of the strands is indicated in the order sense/antisense. Thus, for example, a DNA/RNA hybrid, noted as D/R, is a oligonucleotide the sense strand of which is of a DNA nature and the antisense strand of which is of a RNA nature and of a sequence complementary to the messenger RNA.

In the experiments described, the oligonucleotides whose sequence is indicated below were used.

For the GFP:

GFP:

```
                                    (SEQ ID NO. 29)
    Sense:   [GCAAGCTGACCCTGAAGTTCAT]DNA (SEQ ID NO. 30)
    Anti:    [GAACUUCAGGGUCAGCUUGCCG]RNA
```

Control GFP:

```
                                    (SEQ ID NO. 31)
Sense:       [CAUGUCAUGUGUCACAUCUC]RNA[TT]DNA (SEQ ID NO. 32)
Antisense:   [GAGAUGUGACACAUGACAUG]RNA[TT]DNA
```

FOR THE LNCaP: The underlined bases below correspond to the mutation of the androgen receptor expressed in the cells of human prostate carcinoma (LNCaP).

LNCaP:

```
                                    (SEQ ID NO. 33)
Sense:       [GCATCAGTTCGCTTTTGACTT]DNA (SEQ ID NO. 34)
             [GCAUCAGUUCGCUUUUGAC]RNA-TT [DNA]
```

```
                                    -continued
                                               (SEQ ID NO. 35)
Antisense:      [GTCAAAAGCGAACTGATGCTT]DNA (SEQ ID NO. 36)
                [GUCAAAAGCGAACUGAUGC]RNA=TT [DNA]
```

Control LNCaP:

```
                                               (SEQ ID NO. 37)
Sense:          [GUUCGGUCUGCUUACACUA]RNA-TT [DNA]

(SEQ ID NO. 38)
Antisense:      [UAGUGUAAGCAGACCGAAC]RNA-TT [DNA]
```

For p53:

The DNA of the hybrids noted H1 comprise RNA bases (U, underlined).

The mutation present in the MT1 oligonucleotides is indicated in italics.

```
UWT:
                                               (SEQ ID NO. 39)
  Sense:   5' [GCAUGAACCGGAGGCCCAU]RNA[TT]DNA (SEQ ID NO. 40)
  Anti:    5' [AUGGGCCUCCGGUUCAUGC]RNA[TT]DNA WT H1 D/R:
                                               (SEQ ID NO. 41)
  Sense:   5' [GCAUGAACCGGAGGCCCAUTT]DNA (SEQ ID NO. 42)
  Anti:    5' [AUGGGCCUCCGGUUCAUGC]RNA[TT]DNA WT H1 R/D:
                                               (SEQ ID NO. 43)
  Sense:   5' [GCAUGAACCGGAGGCCCAU]RNA[TT]DNA (SEQ ID NO. 44)
  Anti:    5' [AUGGGCCUCCGGUUCAUGCTT]DNA WT H2 R/D:
                                               (SEQ ID NO. 45)
  Sense:   5' [GCATGAACCGGAGGCCCATTT]DNA (SEQ ID NO. 46)
  Anti:    5' [AUGGGCCYCCGGUUCAYGC]RNA[TT]DNA WT H2 R/D:
                                               (SEQ ID NO. 47)
  Sense:   5' [GCAUGAACCGGAGGCCCAU]RNA[TT]DNA (SEQ ID NO. 48)
  Anti:    5' [ATGGGCCUTCCGGTTCATGCTT]DNA MT1 (R248W) **:
                                               (SEQ ID NO. 49)
  Sense:   5' [GCAUGAACUGGAGGCCCAU]RNA[TT]DNA (SEQ ID NO. 50)
  Anti:    5' [AUGGGCCUCCAAGUUCAUGC]RNA[TT]DNA MT1 H1 D/R:
                                               (SEQ ID NO. 51)
  Sense:   5' [GCAUGAACUUGGAGGCCCAUTT]DNA (SEQ ID NO. 52)
  Anti:    5' [AUGGGCCUCCAAGUUCAUGC]RNA[TT]DNA MT1 H1 R/D:
                                               (SEQ ID NO. 53)
  Sense:   5' [GCAUGAACUGGAGGCCAU]RNA[TT]DNA (SEQ ID NO. 54)
```

```
                                               -continued
  Anti:    5' [AUGGGCCUCCAAGUUCAUGCTT]DNA MT1 H2 DIR:
                                               (SEQ ID NO. 55)
  Sense:   5' [GCATGAACUUTGGAGGCCCATTT]DNA (SEQ ID NO. 56)
  Anti:    5' [AUGGGCCUCCAAGUUCAUGC]RNA[TT]DNA MT1 H2 R/D:
                                               (SEQ ID NO. 57)
  Sense:   5' [GCATGAACUUTGGAGGCCCAT]RNA[TT]DNA (SEQ ID NO. 58)
  Anti:    5' [AUGGGCCUCCAAGUUCAUGCTT]DNA
```

II—Results

1) Inhibition of the GFP (Green Fluorescent Protein) by the DNA/RNA hybrids

The control siRNAs (R/R) or GFP (D/R) in increasing doses were introduced by transfection using the Polyfect kit in C2C12 mouse myoblasts at the same time as a GFP expression vector. The GFP level was monitored by Western blot (FIG. 7A) and by direct measurement of the fluorescence emitted by the GFP by means of a fluorometer (FIG. 7B). There was seen a strong inhibition (up to 80%) of the expression of GFP by the DNA/RNA hybrid siRNAs.

2) Inhibition of the Androgen Receptor by the DNA/RNA Hybrids

FIG. 7D shows that the H1 D/R hybrids are as effective as the R/R for inhibiting the expression of genes. H1299-NCI cells, which do not express p53, were transfected (using lipofectamine) by vectors of expression (400 ng) of wild p53 (WT), mutated p53 (MT) or a mixture of the two (WT+MT), as indicated. A CMV-GFP vector was also transfected as internal control. The siRNAs (400 ng) directed against the wild form (WT), the mutated form (MT) or an irrelevant siRNA (CTRL) were transfected at the same time. The cells were collected 24 hours later and analyzed by Western blot with an antibody directed against p53 (D01, Santa Cruz) or GFP (Santa-Cruz) to monitor the transfection efficacy. Note: the expression of the mutated form of the protein stabilizes the wild form.

FIG. 7E shows that the H2 D/R hybrids were as effective as the R/R for inhibiting the expression of the genes. The H1299-NCI cells, which do not express p53, were transfected (using lipofectamine) by expression vectors (400 ng) of wild p53 (WT), mutated p53 (MT) and a mixture of the two (WT+MT) as indicated. The siRNAs (400 ng) directed against the wild form (WT), the mutated form (MT) or an irrelevant siRNA (C) were transfected at the same time. The cells were collected 24 hours later and analyzed by Western blot with an antibody directed against p53 (D01, Santa Cruz).

EXAMPLE 8

Administration In Vivo of siRNA Via Different Routes

Tumor cells expressing luciferase in a stable manner were injected subcutaneously to nude mice (1 million cells in the right flank). On the 8$^{th}$ day of tumor growth, the tumors having an average volume of 200 mm$^3$ were injected either with control siRNAs (mixed sequence of HIF1α, see example 3) or with a siRNA directed against luciferase. The control siRNAs (3 µg/mouse) were injected in a volume of 50 µl in PBS via the subcutaneous route in the animal's flank.

The luciferase siRNAs were injected at the rate of 3 µg/mouse (3 animals in each group) in 50 µl of PBS via the subcutaneous route (sc), the intraperitoneal route (ip), the intravenous route (iv) (tail vein) or the intratumoral route (it). In this latter case, the luciferase siRNAs (3 µg/mouse) were diluted in only 20 µl of PBS.

Three days after injection of the siRNAs, the animals were sacrificed, the tumors were collected and homogenized with a Polytron grinder. Quantitative determination of the proteins and measurement of the luciferase activity in a luminometer were performed on the homogenates.

The results shown in FIG. 8 show the luciferase activity in relation to the quantity of protein.

Key to Attachment A, Table 2 (pages 44-46 of original French document)
Tableau 2=Table 2
Annexe A=Attachment A
Table headings: Disease/Fusion protein/Chromosomal translocation/Reference Contents of table in English.
Key to Attachment B, Table 3 (pages 47-56 of original French document)
Tableau 3=Table 3
Annexe B=Attachment B
All text in English.
Key to Attachment C, Table 5 (pages 57-100 of original French document)
Tableau 5=Table 5
Annexe C=Attachment C
Table headings and contents in English.
Key to figures (pages 1/14 to 14/14)

Sheet 2/14
contrôle=control
FIG. 2B: at left: VEGF secreted, % of control; at bottom: Days after transfection
FIG. 2C: at left: Tumor volume (mm³); at bottom: Days after injection
FIG. 2D: at left, top row: Nontransfected Sheet 3/14
contrôle=control, sans=without
FIG. 2E: At left: control tumor; At right: siRNA VEGF tumors
FIG. 3: At left: luciferase activity (arbitrary units); legend: normoxia/hypoxia Sheet 4/14
contrôle=control, sans =without
FIG. 4B: At left: relative luciferase activity (arbitrary units); legend: without androgens/androgens
FIG. 4C: At left: Response to the androgens (% of control)

Sheet 5/14
contrôle=control, sans =without; récepteur androgène=androgen receptor
FIG. 4D: At left: Tumor volume (cm³); At bottom: Growth time (days)
FIG. 4E: At left: Tumor volume (cm³); At bottom: Growth time
FIG. 4F: At left: Tumor volume (cm³); At bottom: Growth time (days)

Sheet 8/14
contrôle=control

Sheet 10/14
suite=continuation

Sheet 12/14
contrôle=control
FIG. 7B: At left: GFP (% of the control)
FIG. 7C: At left: Luciferase activity (% of the control)

Sheet 14/14
contrôle=control
FIG. 8: At left: Luciferase activity (arbitrary units)/mg prot
Key to SEQUENCE LISTINGS (pages 1/26 to 26/26)
Sheet 1/26

SEQUENCE LISTING

<110> NATIONAL CENTER OF SCIENTIFIC RESEARCH
<120> Inhibitory oligonucleotides and their use for repressing specifically a gene
<223> Sequence of the gene p53

Sheet 4/26
<223> sense strand of PML-rare
<223> added thymine residues
<223> antisense strand of PML-rare
<223> added thymine residues
<223> sense strand of PML-rare Sheet 5/26
<223> added thymine residues
<223> antisense strand of PML-rare
<223> added thymine residues
<223> sequence stemming from human VEGF
<223> added thymine residues
<223> sequence stemming from human VEGF
<223> added thymine residues Sheet 6/26
<223> sequence stemming from human VEGF
<223> added thymine residues
<223> sequence stemming from human VEGF
<223> added thymine residues
<223> sequence stemming from human HIF1α
<223> added thymine residues
<223> sequence stemming from human HIF1α

Sheet 7/26
<223> added thymine residues
<223> sequence stemming from human HIF1α
<223> added thymine residues
<223> sequence stemming from human HIF1α
<223> sequence stemming from human HIF1α
<223> sequence stemming from the human androgen receptor
<223> added thymine residues Sheet 8/26
<223> sequence stemming from human HIF1α
<223> added thymine residues
<223> sequence stemming from human HIF1α
<223> added thymine residues
<223> sequence stemming from human HIF1α
<223> added thymine residues
<223> sequence stemming from the human androgen receptor bearing mutation T8 77A
<223> added thymine residues Sheet 9/26
<223> sequence stemming from the human androgen receptor bearing mutation T8 77A
<223> added thymine residues
<223> sequence stemming from wild human p53 (sense)

<223> added thymine residues
<223> sequence stemming from wild human p53 (antisense)
<223> added thymine residues Sheet 10/26
<223> sequence stemming from mutated human p53 bearing the mutation MT1 (r248w) (sense)
<223> added thymine residues
<223> sequence stemming from mutated human p53 bearing the mutation MT1 (r248w) (antisense)
<223> added thymine residues
<223> sequence stemming from mutated human p53 bearing the mutation MT2 (r248w) (sense)
<223> added thymine residues
<223> sequence stemming from mutated human p53 bearing the mutation MT2 (r248w) (antisense)

Sheet 11/26
<223> added thymine residues
<223> sequence stemming from E6 of HPV (sense)
<223> added thymine residues
<223> sequence stemming from E6 of HPV (antisense)
<223> sequence stemming from the gene coding GFP (sense strand)
<223> sequence stemming from the gene coding GFP (antisense strand)

Sheet 12/26
<223> sequence stemming from the gene coding GFP (sense strand)
<223> added thymine residues
<223> sequence stemming from the gene coding GFP (antisense strand)
<223> added thymine residues
<223> sequence stemming from the mutated human androgen receptor (sense strand)
<223> sequence stemming from the mutated human androgen receptor (sense strand)

Sheet 13/26
<223> added thymine residues
<223> sequence stemming from the mutated human androgen receptor (sense strand)
<223> sequence stemming from the mutated human androgen receptor (sense strand)
<223> added thymine residues
<223> sequence stemming from the mutated human androgen receptor (sense strand)
<223> added thymine residues Sheet 14/26
<223> sequence stemming from the mutated human androgen receptor (antisense strand)
<223> added thymine residues
<223> sequence stemming from the wild human p53 gene (sense strand)
<223> added thymine residues
<223> sequence stemming from the wild human p53 gene (antisense strand)
<223> added thymine residues
<223> sequence stemming from the mutated human p53 gene (sense strand)
<223> added thymine residues Sheet 15/26
<223> sequence stemming from the wild human p53 gene (antisense strand)
<223> added thymine residues
<223> sequence stemming from the mutated p53 gene (sense strand)
<223> added thymine residues
<223> sequence stemming from the mutated human p53 gene (antisense strand)
<223> added thymine residues
<223> sequence stemming from the mutated p53 gene (sense strand)

Sheet 16/26
<223> added thymine residues
<223> sequence stemming from the mutated human p53 gene (antisense strand)
<223> added thymine residues
<223> sequence stemming from the mutated p53 gene (sense strand)
<223> added thymine residues
<223> sequence stemming from the mutated human p53 gene (antisense strand)
<223> added thymine residues Sheet 17/26
<223> sequence stemming from the mutated p53 gene (sense strand)
<223> added thymine residues
<223> sequence stemming from the mutated human p53 gene (antisense strand)
<223> added thymine residues
<223> sequence stemming from the mutated p53 gene (sense strand)
<223> added thymine residues
<223> sequence stemming from the mutated human p53 gene (antisense strand)

Sheet 18/26
<223> added thymine residues
<223> sequence stemming from the mutated human p53 gene (sense strand)
<223> added thymine residues
<223> sequence stemming from the mutated human p53 gene (antisense strand)
<223> added thymine residues
<223> sequence stemming from the mutated human p53 gene (sense strand)
<223> added thymine residues Sheet 19/26
<223> sequence stemming from the mutated human p53 gene (antisense strand)
<223> added thymine residues
<223> sequence stemming from the mutated human p53 gene (sense strand)
<223> added thymine residues
<223> sequence stemming from the mutated human p53 gene (antisense strand)
<223> added thymine residues
<223> Homo sapiens hypoxia-inducible factor 1 subunit alpha (HIF1α)

Sheet 21/26
<223> human VEGF A

Sheet 22/26
<223> sequence stemming from the human wild gene p53
<223> sequence stemming from the human wild gene p53
<223> sequence stemming from the human wild gene p53
<223> sequence stemming from the human wild gene p53

Sheet 23/26
<223> sequence stemming from the human wild gene p53
<223> sequence stemming from the human wild gene p53
<223> sequence stemming from the human wild gene p53

<223> sequence stemming from the human wild gene p53
<223> sequence stemming from the human mutated gene p53 bearing the mutation r273h Sheet 24/26
<223> sequence stemming from the human mutated gene p53 bearing the mutation r248q
<223> sequence stemming from the human mutated gene p53 bearing the mutation r248w
<223> sequence stemming from the human mutated gene p53 bearing the mutation r249s <223> sequence stemming from the human mutated gene p53 bearing the mutation g245s
<223> sequence stemming from the human mutated gene p53 bearing the mutation r282w
<223> sequence stemming from the human mutated gene p53 bearing the mutation r175h Sheet 25/26
<223> sequence stemming from the human mutated gene p53 bearing the mutation c242s
<223> sequence coding for the human androgen receptor

SEQUENCE LISTING

<160> NUMBER OF SEQ ID NOS: 77

<210> SEQ ID NO 1
<211> LENGTH: 1182
<212> TYPE: DNA
<213> ORGANISM: Homo sapiens
<220> FEATURE:
<221> NAME/KEY: misc_feature
<222> LOCATION: (1)..(1182)
<223> OTHER INFORMATION: sequence of the gene p53

<400> SEQUENCE: 1

```
atggaggagc cgcagtcaga tcctagcgtc gagccccctc tgagtcagga aacatttca      60 gacctatgga aactacttcc tgaaaacaac gttctgtccc ccttgccgtc ccaagcaatg     120
gatgatttga tgctgtcccc ggacgatatt gaacaatggt tcactgaaga cccaggtcca    180
gatgaagctc ccagaatgcc agaggctgct cccccgtgg ccctgcacc agcagctcct     240 acaccggcgg cccctgcacc agcccctcc tggcccctgt catcttctgt ccttcccag      300 aaaacctacc agggcagcta cggtttccgt ctgggcttct tgcattctgg gacagccaag    360
tctgtgactt gcacgtactc ccctgccctc aacaagatgt tttgccaact ggccaagacc    420
tgccctgtgc agctgtgggt tgattccaca ccccgcccg caccgcgt ccgcgccatg       480 gccatctaca agcagtcaca gcacatgacg gaggttgtga ggcgctgccc ccaccatgag    540
cgctgctcag atagcgatgg tctggcccct cctcagcatc ttatccgagt ggaaggaaat    600
ttgcgtgtgg agtatttgga tgacagaaac acttttcgac atagtgtggt ggtgccctat    660
gagccgcctg aggttggctc tgactgtacc accatccact acaactacat gtgtaacagt    720
tcctgcatgg gcggcatgaa ccggaggccc atcctcacca tcatcacact ggaagactcc    780
agtggtaatc tactgggacg gaacagcttt gaggtgcgtg tttgtgcctg tcctgggaga    840
gaccggcgca cagaggaaga gaatctccgc aagaaggggg agcctcacca cgagctgccc    900
ccagggagca ctaagcgagc actgcccaac aacaccagct cctctcccca gccaaagaag    960
aaaccactgg atggagaata tttcaccctt cagatccgtg ggcgtgagcg cttcgagatg   1020
ttccgagagc tgaatgaggc cttggaactc aaggatgccc aggctgggaa ggagccaggg   1080
gggagcaggg ctcactccag ccacctgaag tccaaaaagg gtcagtctac ctcccgccat   1140
aaaaaactca tgttcaagac agaagggcct gactcagact ga                        1182
```

<210> SEQ ID NO 2
<211> LENGTH: 7904
<212> TYPE: DNA
<213> ORGANISM: Homo sapiens
<220> FEATURE:
<221> NAME/KEY: misc_feature
<222> LOCATION: (1)..(7904)
<223> OTHER INFORMATION: variant HPV16

-continued

```
<400> SEQUENCE: 2
actacaataa ttcatgtata aaactaaggg cgtaaccgaa atcggttgaa ccgaaaccgg      60
ttagtataaa agcagacatt ttatgcacca aaagagaact gcaatgtttc aggacccaca    120
ggagcgaccc agaaagttac cacagttatg cacagagctg caaacaacta tacatgatat    180
aatattagaa tgtgtgtact gcaagcaaca gttactgcga cgtgaggtat atgactttgc    240
ttttcgggat ttatgcatag tatatagaga tgggaatcca tatgctgtat gtgataaatg    300
tttaaagttt tattctaaaa ttagtgagta tagacattat tgtttatagtt tgtatggaac    360 aacattagaa cagcaataca acaaaccgtt gtgtgatttg ttaattaggt gtattaactg    420
tcaaaagcca ctgtgtcctg aagaaaagca aagacatctg gacaaaaagc aaagattcca    480
taatataagg ggtcggtgga ccggtcgatg tatgtcttgt tgcagatcat caagaacacg    540
tagagaaacc cagctgtaat catgcatgga gatacaccta cattgcatga atatatgtta    600
gatttgcaac cagagacaac tgatctctac tgttatgagc aattaaatga cagctcagag    660
gaggaggatg aaatagatgg tccagctgga caagcagaac cggacagagc ccattacaat    720
attgtaacct tttgttgcaa gtgtgactct acgcttcggt tgtgcgtaca aagcacacac    780
gtagacattc gtactttgga agacctgtta atgggcacac taggaattgt gtgccccatc    840
tgttctcaga aaccataatc taccatggct gatcctgcag gtaccaatgg ggaagagggt    900
acgggatgta atgatggtt ttatgtagag gctgtagtgg aaaaaaaaac aggggatgct    960
atatcagatg acgagaacga aaatgacagt gatacaggtg aagatttggt agattttata   1020
gtaaatgata atgattattt aacacaggca gaaacagaga cagcacatgc gttgtttact   1080
gcacaggaag caaacaaca tagagatgca gtacaggttc taaaacgaaa gtatttggta   1140
gtccacttag tgatattagt ggatgtgtag acaataatat tagtcctaga ttaaaagcta   1200
tatgtataga aaaacaaagt agagctgcaa aaggagatt atttgaaagc gaagacagcg   1260
ggtatggcaa tactgaagtg gaaactcagc agatgttaca ggtagaaggg cgccatgaga   1320
ctgaaacacc atgtagtcag tatagtggtg gaagtggggg tggttgcagt cagtacagta   1380
gtggaagtgg gggagagggt gttagtgaaa gacacactat atgccaaaca ccacttacaa   1440
atattttaaa tgtactaaaa actagtaatg caaaggcagc aatgttagca aaatttaaag   1500
agttatacgg ggtgagtttt tcagaattag taagaccatt taaaagtaat aaatcaacgt   1560
gttgcgattg gtgtattgct gcatttggac ttacacccag tatagctgac agtataaaaa   1620
cactattaca acaatattgt ttatatttac acattcaaag tttagcatgt tcatggggaa   1680
tggttgtgtt actattagta agatataaat gtggaaaaaa tagagaaaca attgaaaaat   1740
tgctgtctaa actattatgt gtgtctccaa tgtgtatgat gatagagcct ccaaaattgc   1800
gtagtacagc agcagcatta tattggtata aacaggtat atcaaatatt agtgaagtgt   1860
atggagacac gccagaatgg atacaaagac aaacagtatt acaacatagt tttaatgatt   1920
gtacatttga attatcacag atggtacaat gggcctacga taatgacata gtagacgata   1980
gtgaaattgc atataaatat gcacaattgg cagacactaa tagtaatgca agtgcctttc   2040
taaaaagtaa ttcacaggca aaaattgtaa aggattgtgc aacaatgtgt agacattata   2100
aacgagcaga aaaaaaacaa atgagtatga gtcaatggat aaaatataga tgtgataggg   2160
tagatgatgg aggtgattgg aagcaaattg ttatgttttt aaggtatcaa ggtgtagagt   2220
ttatgtcatt tttaactgca ttaaaaagat ttttgcaagg catacctaaa aaaaattgca   2280
```

-continued

```
tattactata tggtgcagct aacacaggta aatcattatt tggtatgagt ttaatgaaat    2340
ttctgcaagg gtctgtaata tgttttgtaa attctaaaag ccattttggg ttacaaccat    2400
tagcagatgc caaaataggt atgttagatg atgctacagt gccctgttgg aactacatag    2460
atgacaattt aagaaatgca ttggatggaa atttagtttc tatggatgta aagcatagac    2520
cattggtaca actaaaatgc cctccattat taattcatc taacattaat gctggtacag     2580
attctaggtg gccttattta cataatagat tggtggtgtt tacatttcct aatgagtttc    2640
catttgacga aaacggaaat ccagtgtatg agcttaatga taagaactgg aaatcctttt    2700
tctcaaggac gtggtccaga ttaagtttgc acgaggacga ggacaaggaa aacgatggag    2760
actctttgcc aacgtttaaa tgtgtgtcag acaaaatac taacacatta tgaaaatgat      2820
agtacagacc tacgtgacca tatagactat ggaaacaca tgcgcctaga atgtgctatt      2880
tattacaagg ccagagaaat gggatttaaa catattaacc accaagtggt gccaacactg    2940
gctgtatcaa agaataaagc attacaagca attgaactgc aactaacgtt agaaacaata    3000
tataactcac aatatagtaa tgaaaagtgg acattacaag acgttagcct tgaagtgtat    3060
ttaactgcac caacaggatg tataaaaaaa catggatata cagtggaagt gcagtttgat    3120
ggagacatat gcaatacaat gcattataca aactggacac atatatatat ttgtgaagaa    3180
gcatcagtaa ctgtggtaga gggtcaagtt gactattatg gtttatatta tgttcatgaa    3240
ggaatacgaa catattttgt gcagtttaaa gatgatgcag aaaaatatag taaaaataaa    3300
gtatgggaag ttcatgcggg tggtcaggta atattatgtc ctacatctgt gtttagcagc    3360
aacgaagtat cctctcctga aattattagg cagcacttgg ccaaccaccc cgccgcgacc    3420
cataccaaag ccgtcgcctt gggcaccgaa gaaacacaga cgactatcca gcgaccaaga    3480
tcagagccag acaccggaaa cccctgccac accactaagt tgttgcacag agactcagtg    3540
gacagtgctc caatcctcac tgcatttaac agctcacaca aaggacggat taactgtaat    3600
agtaacacta cacccatagt acatttaaaa ggtgatgcta atactttaaa atgtttaaga    3660
tatagattta aaaagcattg tacattgtat actgcagtgt cgtctacatg gcattggaca    3720
ggacataatg taaaacataa aagtgcaatt gttacactta catatgatag tgaatggcaa    3780
cgtgaccaat ttttgtctca agttaaaata ccaaaaacta ttacagtgtc tactggattt    3840
atgtctatat gacaaatctt gatactgcat ccacaacatt actggcgtgc ttttttgcttt   3900 gctttgtgtg cttttgtgtg tctgcctatt aatacgtccg ctgcttttgt ctgtgtctac    3960
atacacatca ttaataatat tggtattact attgtggata acagcagcct ctgcgtttag    4020 gtgtttatt gtatatatta tatttgttta tataccatta tttttaatac atacacatgc      4080
acgcttttta attacataat gtatatgtac ataatgtaat tgttacatat aattgttgta    4140
taccataact tactatttt tcttttttat tttcatatat aattttttt tttgtttgtt      4200 tgtttgtttt ttaataaact gttattactt aacaatgcga cacaaacgtt ctgcaaaacg    4260
cacaaaacgt gcatcggcta cccaacttta taaacatgc aaacaggcag gtacatgtcc     4320
acctgacatt ataccctaagg ttgaaggcaa actattgct gaacaaatat tacaatatgg     4380
aagtatgggt gtatttttg gtgggttagg aattggaaca gggtcgggta caggcggacg     4440
cactgggtat attccattgg gaacaaggcc tcccacagct acagatacac ttgctcctgt    4500 aagacccct ttaacagtag atcctgtggg cccttctgat ccttctatag tttctttagt     4560
ggaagaaact agtttattg atgctggtgc accaacatct gtaccttcca ttcccccaga    4620
tgtatcagga tttagtatta ctacttcaac tgataccaca cctgctatat tagatattaa    4680
```

-continued

```
taatactgtt actactgtta ctacacataa taatcccact ttcactgacc catctgtatt   4740
 
gcagcctcca acacctgcag aaactggagg gcattttaca ctttcatcat ccactattag   4800
tacacataat tatgaagaaa ttcctatgga tacatttatt gttagcacaa accctaacac   4860
agtaactagt agcacaccca taccagggtc tcgcccagtg gcacgcctag gattatatag   4920
tcgcacaaca caacaggtta aagttgtaga ccctgctttt gtaaccactc ccactaaact   4980
tattacatat gataatcctg catatgaagg tatagatgtg gataatacat tatatttttc   5040
tagtaatgat aatagtatta atatagctcc agatcctgac tttttggata tagttgcttt   5100
acataggcca gcattaacct ctaggcgtac tggcattagg tacagtagaa ttggtaataa   5160
acaaacacta cgtactcgta gtggaaaatc tataggtgct aaggtacatt attattatga   5220
tttaagtact attgatcctg cagaagaaat agaattacaa actataacac cttctacata   5280
tactaccact tcacatgcag cctcacctac ttctattaat aatggattat atgatattta   5340
tgcagatgac tttattacag atacttctac aaccccggta ccatctgtac cctctacatc   5400
tttatcaggt tatattcctg caaatacaac aattcctttt ggtggtgcat acaatattcc   5460
tttagtatca ggtcctgata tacccattaa tataactgac caagctcctt cattaattcc   5520
tatagttcca gggtctccac aatatacaat tattgctgat gcaggtgact tttatttaca   5580
tcctagttat tacatgttac gaaaacgacg taaacgttta ccatattttt tttcagatgt   5640
ctctttggct gcctagtgag gccactgtct acttgcctcc tgtcccagta tctaaggttg   5700
taagcacgga tgaatatgtt gcacgcacaa acatatatta tcatgcagga acatccagac   5760
tacttgcagt tggacatccc tattttccta ttaaaaaacc taacaataac aaaatattag   5820
ttcctaaagt atcaggatta caatacaggg tatttagaat acatttacct gaccccaata   5880
agtttggttt tcctgacacc tcattttata atccagatac acagcggctg gtttgggcct   5940
gtgtaggtgt tgaggtaggt cgtggtcagc cattaggtgt gggcattagt ggccatcctt   6000
tattaaataa attggatgac acagaaaatg ctagtgctta tgcagcaaat gcaggtgtgg   6060
ataatagaga atgtatatct atggattaca aacaaacaca attgtgttta attggttgca   6120
aaccacctat aggggaacac tggggcaaag gatccccatg taccaatgtt gcagtaaatc   6180
caggtgattg tccaccatta gagttaataa acacagttat tcaggatggt gatatggttc   6240
atactggctt tggtgctatg gactttacta cattacaggc taacaaaagt gaagttccac   6300
tggatatttg tacatctatt tgcaaatatc cagattatat taaaatggtg tcagaaccat   6360
atggcgacag cttatttttt tatttacgaa gggaacaaat gtttgttaga catttattta   6420
atagggctgg tactgttggt gaaaatgtac cagacgattt atacattaaa ggctctgggt   6480
ctactgcaaa tttagccagt tcaaattatt ttcctacacc tagtggttct atggttacct   6540
ctgatgccca aatattcaat aaaccttatt ggttacaacg agcacagggc cacaataatg   6600
gcatttgttg ggggtaaccaa ctatttgtta ctgttgttga tactacacgc agtacaaata   6660
tgtcattatg tgctgccata tctacttcag aaactacata taaaaatact aactttaagg   6720
agtacctacg acatggggag gaatatgatt tacagtttat ttttcaactg tgcaaaataa   6780
ccttaactgc agacgttatg acatacatac attctatgaa ttccactatt ttggaggact   6840
ggaattttgg tctacaacct cccccaggag gcacactaga agatacttat aggtttgtaa   6900
cccaggcaat tgcttgtcaa aaacatacac ctccagcacc taaagaagat gatcccctta   6960
aaaaatacac tttttgggaa gtaaatttaa aggaaaagtt ttctgcagac ctagatcagt   7020
```

```
ttcctttagg acgcaaattt ttactacaag caggattgaa ggccaaacca aaatttacat    7080
taggaaaacg aaaagctaca cccaccacct catctacctc tacaactgct aaacgcaaaa    7140
aacgtaagct gtaagtattg tatgtatgtt gaattagtgt tgtttgttgt gtatatgttt    7200
gtatgtgctt gtatgtgctt gtaaatatta agttgtatgt gtgtttgtat gtatggtata    7260
ataaacacgt gtgtatgtgt ttttaaatgc ttgtgtaact attgtgtcat gcaacataaa    7320
taaacttatt gtttcaacac ctactaattg tgttgtggtt attcattgta tataaactat    7380
atttgctaca tcctgttttt gttttatata tactatattt tgtagcgcca ggcccatttt    7440
gtagcttcaa ccgaattcgg ttgcatgctt tttggcacaa aatgtgtttt tttaaatagt    7500
tctatgtcag caactatggt ttaaacttgt acgtttcctg cttgccatgc gtgccaaatc    7560
cctgttttcc tgacctgcac tgcttgccaa ccattccatt gttttttaca ctgcactatg    7620
tgcaactact gaatcactat gtacattgtg tcatataaaa taaatcacta tgcgccaacg    7680
ccttacatac cgctgttagg cacatatttt tggcttgttt taactaacct aattgcatat    7740
ttggcataag gtttaaactt ctaaggccaa ctaaatgtca ccctagttca tacatgaact    7800
gtgtaaaggt tagtcataca ttgttcattt gtaaaactgc acatgggtgt gtgcaaaccg    7860
attttgggtt acacatttac aagcaactta tataataata ctaa                     7904
```

<210> SEQ ID NO 3
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: sense strand of PML-rare
<220> FEATURE:
<221> NAME/KEY: misc_feature
<222> LOCATION: (21)..(22)
<223> OTHER INFORMATION: added thymine residues

<400> SEQUENCE: 3
caugucaugu gucacaucuc tt                                              22

<210> SEQ ID NO 4
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: antisense strand of PML-rare
<220> FEATURE:
<221> NAME/KEY: misc_feature
<222> LOCATION: (21)..(22)
<223> OTHER INFORMATION: added thymine residues

<400> SEQUENCE: 4
gagaugugac acaugacaug tt                                              22

```
<210> SEQ ID NO 5
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: sense strand of PML-rare
<220> FEATURE:
<221> NAME/KEY: misc_feature
<222> LOCATION: (21)..(22)
<223> OTHER INFORMATION: added thymine residues

<400> SEQUENCE: 5
ggggaggcag ccauugagac tt                                              22

<210> SEQ ID NO 6
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: antisense strand of PML-rare
<220> FEATURE:
<221> NAME/KEY: misc_feature
<222> LOCATION: (21)..(22)
<223> OTHER INFORMATION: added thymine residues

<400> SEQUENCE: 6
gucucaaugg cugccucccc tt                                              22

<210> SEQ ID NO 7
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(21)
<223> OTHER INFORMATION: sequence stemming from human VEGF
<220> FEATURE:
<221> NAME/KEY: misc_feature
<222> LOCATION: (22)..(23)
<223> OTHER INFORMATION: added thymine residues

<400> SEQUENCE: 7
augugaaugc agaccaaaga att                                             23

<210> SEQ ID NO 8
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
```

```
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(21)
<223> OTHER INFORMATION: sequence stemming from human VEGF
<220> FEATURE:
<221> NAME/KEY: misc_feature
<222> LOCATION: (22)..(23)
<223> OTHER INFORMATION: added thymine residues

<400> SEQUENCE: 8
uucuuugguc ugcauucaca utt                                              23

<210> SEQ ID NO 9
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: sequence stemming from human VEGF
<220> FEATURE:
<221> NAME/KEY: misc_feature
<222> LOCATION: (21)..(22)
<223> OTHER INFORMATION: added thymine residues

<400> SEQUENCE: 9
caugucaugu gucacaucuc tt                                               22

<210> SEQ ID NO 10
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: sequence stemming from human VEGF
<220> FEATURE:
<221> NAME/KEY: misc_feature
<222> LOCATION: (21)..(22)
<223> OTHER INFORMATION: added thymine residues

<400> SEQUENCE: 10
gagaugugac acaugacaug tt                                               22

<210> SEQ ID NO 11
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(21)
<223> OTHER INFORMATION: sequence stemming from human HIF1-alpha
```

-continued

```
<220> FEATURE:
<221> NAME/KEY: misc_feature
<222> LOCATION: (22)..(23)
<223> OTHER INFORMATION: added thymine residues

<400> SEQUENCE: 11
caugugacca ugaggaaaug att                                              23

<210> SEQ ID NO 12
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(21)
<223> OTHER INFORMATION: sequence stemming from human HIF1-alpha
<220> FEATURE:
<221> NAME/KEY: misc_feature
<222> LOCATION: (22)..(23)
<223> OTHER INFORMATION: added thymine residues

<400> SEQUENCE: 12
ucauuuccuc auggucacau gtt                                              23

<210> SEQ ID NO 13
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(21)
<223> OTHER INFORMATION: sequence stemming from human HIF1-alpha
<220> FEATURE:
<221> NAME/KEY: misc_feature
<222> LOCATION: (22)..(23)
<223> OTHER INFORMATION: added thymine residues

<400> SEQUENCE: 13
gauagcaaug acgaaugcgu att                                              23

<210> SEQ ID NO 14
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(21)
<223> OTHER INFORMATION: sequence stemming from human HIF1-alpha
<220> FEATURE:
<221> NAME/KEY: misc_feature
<222> LOCATION: (22)..(23)
<223> OTHER INFORMATION: added thymine residues

<400> SEQUENCE: 14
```
uacgcauucg ucauugcuau ctt                              23

<210> SEQ ID NO 15
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(21)
<223> OTHER INFORMATION: sequence stemming from human androgen receptor
<220> FEATURE:
<221> NAME/KEY: misc_feature
<222> LOCATION: (22)..(23)
<223> OTHER INFORMATION: added thymine residues

<400> SEQUENCE: 15
gacucagcug ccccauccac gtt                              23

<210> SEQ ID NO 16
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(21)
<223> OTHER INFORMATION: sequence stemming from human HIF1-alpha
<220> FEATURE:
<221> NAME/KEY: misc_feature
<222> LOCATION: (22)..(23)
<223> OTHER INFORMATION: added thymine residues

<400> SEQUENCE: 16
cguggauggg gcagcugagu ctt                              23

<210> SEQ ID NO 17
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(21)
<223> OTHER INFORMATION: sequence stemming from human HIF1-alpha
<220> FEATURE:
<221> NAME/KEY: misc_feature
<222> LOCATION: (22)..(23)
<223> OTHER INFORMATION: added thymine residues

<400> SEQUENCE: 17
gauagcaaug acgaaugcgu att                              23

<210> SEQ ID NO 18
<211> LENGTH: 23
<212> TYPE: DNA
<213> ORGANISM: Artificial Sequence -continued

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(21)
<223> OTHER INFORMATION: sequence stemming from human HIF1-alpha
<220> FEATURE:
<221> NAME/KEY: misc_feature
<222> LOCATION: (22)..(23)
<223> OTHER INFORMATION: added thymine residues

<400> SEQUENCE: 18
uacgcauucg ucauugcuau ctt                                              23

<210> SEQ ID NO 19
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from human androgen receptor
      bearing
      mutation T8 77A
<220> FEATURE:
<221> NAME/KEY: misc_feature
<222> LOCATION: (20)..(21)
<223> OTHER INFORMATION: added thymine residues

<400> SEQUENCE: 19
gcaucaguuc gcuuuugact t                                                21

<210> SEQ ID NO 20
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from human androgen receptor
      bearing
      mutation T8 77A
<220> FEATURE:
<221> NAME/KEY: misc_feature
<222> LOCATION: (20)..(21)
<223> OTHER INFORMATION: added thymine residues

<400> SEQUENCE: 20
gucaaaagcg aacugaugct t                                                21

<210> SEQ ID NO 21
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
```

```
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from wild human p53 (sense)
<220> FEATURE:
<221> NAME/KEY: misc_feature
<222> LOCATION: (20)..(21)
<223> OTHER INFORMATION: added thymine residues

<400> SEQUENCE: 21
gcaugaaccg gaggcccaut t                                                  21

<210> SEQ ID NO 22
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from wild human p53
      (antisense)
<220> FEATURE:
<221> NAME/KEY: misc_feature
<222> LOCATION: (20)..(21)
<223> OTHER INFORMATION: added thymine residues

<400> SEQUENCE: 22
augggccucc gguucaugct t                                                  21

<210> SEQ ID NO 23
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from muatated human p53
      bearing the mutation MT1 (r248w)(sense)
<220> FEATURE:
<221> NAME/KEY: misc_feature
<222> LOCATION: (20)..(21)
<223> OTHER INFORMATION: added thymine residues

<400> SEQUENCE: 23
gcaugaacug gaggcccaut t                                                  21

<210> SEQ ID NO 24
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
```

```
<222> LOCATION: (1)..(19)
<223> OTHER INFORMATION: sequence stemming from muatated human p53
      bearing the mutation
      MT1 (r248w)(antisense)
<220> FEATURE:
<221> NAME/KEY: misc_feature
<222> LOCATION: (20)..(21)
<223> OTHER INFORMATION: added thymine residues

<400> SEQUENCE: 24
augggccucc aguucaugct t                                              21

<210> SEQ ID NO 25
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from muatated human p53
      bearing the mutation MT2 (r248w)(sense)
<220> FEATURE:
<221> NAME/KEY: misc_feature
<222> LOCATION: (20)..(21)
<223> OTHER INFORMATION: added thymine residues

<400> SEQUENCE: 25
ucaugaacug gaggcccaut t                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from muatated human p53
      bearing the mutation MT2 (r248w)(antisense)
<220> FEATURE:
<221> NAME/KEY: misc_feature
<222> LOCATION: (20)..(21)
<223> OTHER INFORMATION: added thymine residues

<400> SEQUENCE: 26
augggccucc aguucaugat t                                              21

<210> SEQ ID NO 27
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from E6 of HPV (sense)
<220> FEATURE:
```

```
<221> NAME/KEY: misc_feature
<222> LOCATION: (20)..(21)
<223> OTHER INFORMATION: added thymine residues

<400> SEQUENCE: 27
ccacaguuau gcacagagct t                                              21

<210> SEQ ID NO 28
<211> LENGTH: 20
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: sequence stemming from E6 of HPV (antisense)
<220> FEATURE:
<221> NAME/KEY: misc_feature
<222> LOCATION: (19)..(20)
<223> OTHER INFORMATION: added thymine residues

<400> SEQUENCE: 28
gcucugugca uaacuuggtt                                                20

<210> SEQ ID NO 29
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(22)
<223> OTHER INFORMATION: sequence stemming from the gene coding GFP
      (sense strand)

<400> SEQUENCE: 29
gcaagctgac cctgaagttc at                                             22

<210> SEQ ID NO 30
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(22)
<223> OTHER INFORMATION: sequence stemming from the gene coding GFP
      (antisense strand)

<400> SEQUENCE: 30
gaacuucagg gucagcuugc cg                                             22

<210> SEQ ID NO 31
<211> LENGTH: 22
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: sequence stemming from the gene coding GFP
      (sense strand)
<220> FEATURE:
<221> NAME/KEY: misc_feature
<222> LOCATION: (21)..(22)
<223> OTHER INFORMATION: added thymine residues

<400> SEQUENCE: 31
caugucaugu gucacaucuc tt                                                   22

<210> SEQ ID NO 32
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: sequence stemming from the gene coding GFP
      (antisense strand)
<220> FEATURE:
<221> NAME/KEY: misc_feature
<222> LOCATION: (21)..(22)
<223> OTHER INFORMATION: added thymine residues

<400> SEQUENCE: 32
gagaugugac acaugacaug tt                                                   22

<210> SEQ ID NO 33
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(21)
<223> OTHER INFORMATION: sequence stemming from the mutated human
      androgen receptor (sense strand)

<400> SEQUENCE: 33
gcatcagttc gcttttgact t                                                    21

<210> SEQ ID NO 34
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
```

```
<222> LOCATION: (1)..(19)
<223> OTHER INFORMATION: sequence stemming from the mutated human
      androgen receptor (sense strand)
<220> FEATURE:
<221> NAME/KEY: misc_feature
<222> LOCATION: (20)..(21)
<223> OTHER INFORMATION: added thymine residues

<400> SEQUENCE: 34
gcaucaguuc gcuuugact t                                          21

<210> SEQ ID NO 35
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(21)
<223> OTHER INFORMATION: sequence stemming from the mutated human
      androgen receptor (sense strand)

<400> SEQUENCE: 35
gtcaaaagcg aactgatgct t                                         21

<210> SEQ ID NO 36
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human
      androgen receptor (sense strand)
<220> FEATURE:
<221> NAME/KEY: misc_feature
<222> LOCATION: (20)..(21)
<223> OTHER INFORMATION: added thymine residues

<400> SEQUENCE: 36
gucaaaagcg aacugaugct t                                         21

<210> SEQ ID NO 37
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human
      androgen receptor (sense strand)
<220> FEATURE:
<221> NAME/KEY: misc_feature
<222> LOCATION: (20)..(21)
<223> OTHER INFORMATION: added thymine residues
```

```
<400> SEQUENCE: 37
guucggucug cuuacacuat t                                              21

<210> SEQ ID NO 38
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human
      androgen receptor (antisense strand)
<220> FEATURE:
<221> NAME/KEY: misc_feature
<222> LOCATION: (20)..(21)
<223> OTHER INFORMATION: added thymine residues

<400> SEQUENCE: 38
uaguguaagc agaccgaact t                                              21

<210> SEQ ID NO 39
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the wild human p53 gene
      (sense strand)
<220> FEATURE:
<221> NAME/KEY: misc_feature
<222> LOCATION: (20)..(21)
<223> OTHER INFORMATION: added thymine residues

<400> SEQUENCE: 39
gcaugaaccg gaggcccaut t                                              21

<210> SEQ ID NO 40
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the wild human p53 gene
      (antisense strand)
<220> FEATURE:
<221> NAME/KEY: misc_feature
<222> LOCATION: (20)..(21)
<223> OTHER INFORMATION: added thymine residues

<400> SEQUENCE: 40
augggccucc gguucaugct t                                              21
```

<210> SEQ ID NO 41
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human p53
      gene (antisense strand)
<220> FEATURE:
<221> NAME/KEY: misc_feature
<222> LOCATION: (20)..(21)
<223> OTHER INFORMATION: added thymine residues

<400> SEQUENCE: 41
gcaugaaccg gaggcccaut t                                            21

<210> SEQ ID NO 42
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human p53
      gene (sense strand)
<220> FEATURE:
<221> NAME/KEY: misc_feature
<222> LOCATION: (20)..(21)
<223> OTHER INFORMATION: added thymine residues

<400> SEQUENCE: 42
augggccucc gguucaugct t                                            21

<210> SEQ ID NO 43
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human p53
      gene(antisense strand)
<220> FEATURE:
<221> NAME/KEY: misc_feature
<222> LOCATION: (20)..(21)
<223> OTHER INFORMATION: added thymine residues

<400> SEQUENCE: 43
gcaugaaccg gaggcccaut t                                            21

<210> SEQ ID NO 44
<211> LENGTH: 21
<212> TYPE: DNA

```
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human p53
      gene(antisense strand)
<220> FEATURE:
<221> NAME/KEY: misc_feature
<222> LOCATION: (20)..(21)
<223> OTHER INFORMATION: added thymine residues

<400> SEQUENCE: 44
augggccucc gguucaugct t                                            21

<210> SEQ ID NO 45
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human p53
      gene(antisense strand)
<220> FEATURE:
<221> NAME/KEY: misc_feature
<222> LOCATION: (20)..(21)
<223> OTHER INFORMATION: added thymine residues

<400> SEQUENCE: 45
gcatgaaccg gaggcccatt t                                            21

<210> SEQ ID NO 46
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human p53
      gene(antisense strand)
<220> FEATURE:
<221> NAME/KEY: misc_feature
<222> LOCATION: (20)..(21)
<223> OTHER INFORMATION: added thymine residues

<400> SEQUENCE: 46
augggccucc gguucaugct t                                            21

<210> SEQ ID NO 47
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
```

```
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human p53
      gene(sense strand)
<220> FEATURE:
<221> NAME/KEY: misc_feature
<222> LOCATION: (20)..(21)
<223> OTHER INFORMATION: added thymine residues

<400> SEQUENCE: 47
gcaugaaccg gaggcccaut t                                                   21

<210> SEQ ID NO 48
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: sequence stemming from the mutated human p53
      gene(antisense strand)
<220> FEATURE:
<221> NAME/KEY: misc_feature
<222> LOCATION: (21)..(22)
<223> OTHER INFORMATION: added thymine residues

<400> SEQUENCE: 48
atgggccutc cggttcatgc tt                                                  22

<210> SEQ ID NO 49
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human p53
      gene (sense strand)
<220> FEATURE:
<221> NAME/KEY: misc_feature
<222> LOCATION: (20)..(21)
<223> OTHER INFORMATION: added thymine residues

<400> SEQUENCE: 49
gcaugaacug gaggcccaut t                                                   21

<210> SEQ ID NO 50
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
```

```
<221> NAME/KEY: misc_feature
<222> LOCATION: (1)..(19)
<223> OTHER INFORMATION: sequence stemming from the mutated human p53
      gene (antisense strand)
<220> FEATURE:
<221> NAME/KEY: misc_feature
<222> LOCATION: (20)..(21)
<223> OTHER INFORMATION: added thymine residues

<400> SEQUENCE: 50
augggccucc aguucaugct t                                              21

<210> SEQ ID NO 51
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human p53
      gene (sense strand)
<220> FEATURE:
<221> NAME/KEY: misc_feature
<222> LOCATION: (20)..(21)
<223> OTHER INFORMATION: added thymine residues

<400> SEQUENCE: 51
gcaugaacug gaggcccaut t                                              21

<210> SEQ ID NO 52
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human p53
      gene (antisense strand)
<220> FEATURE:
<221> NAME/KEY: misc_feature
<222> LOCATION: (20)..(21)
<223> OTHER INFORMATION: added thymine residues

<400> SEQUENCE: 52
augggccucc aguucaugct t                                              21

<210> SEQ ID NO 53
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human p53
      gene (sense strand)
```

```
<220> FEATURE:
<221> NAME/KEY: misc_feature
<222> LOCATION: (20)..(21)
<223> OTHER INFORMATION: added thymine residues

<400> SEQUENCE: 53
gcaugaacug gaggcccaut t                                              21

<210> SEQ ID NO 54
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human p53
      gene (antisense strand)
<220> FEATURE:
<221> NAME/KEY: misc_feature
<222> LOCATION: (20)..(21)
<223> OTHER INFORMATION: added thymine residues

<400> SEQUENCE: 54
augggccucc aguucaugct t                                              21

<210> SEQ ID NO 55
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human p53
      gene (antisense strand)
<220> FEATURE:
<221> NAME/KEY: misc_feature
<222> LOCATION: (20)..(21)
<223> OTHER INFORMATION: added thymine residues

<400> SEQUENCE: 55
gcatgaactg gaggcccatt t                                              21

<210> SEQ ID NO 56
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human p53
      gene (antisense strand)
<220> FEATURE:
<221> NAME/KEY: misc_feature
<222> LOCATION: (20)..(21)
<223> OTHER INFORMATION: added thymine residues
```

```
<400> SEQUENCE: 56
augggccucc aguucaugct t                                              21

<210> SEQ ID NO 57
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human p53
      gene (sense strand)
<220> FEATURE:
<221> NAME/KEY: misc_feature
<222> LOCATION: (20)..(21)
<223> OTHER INFORMATION: added thymine residues

<400> SEQUENCE: 57
gcatgaactg gaggcccatt t                                              21

<210> SEQ ID NO 58
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human p53
      gene(antisense strand)
<220> FEATURE:
<221> NAME/KEY: misc_feature
<222> LOCATION: (20)..(21)
<223> OTHER INFORMATION: added thymine residues

<400> SEQUENCE: 58
augggccucc aguucaugct t                                              21

<210> SEQ ID NO 59
<211> LENGTH: 3933
<212> TYPE: DNA
<213> ORGANISM: Homo sapiens
<220> FEATURE:
<221> NAME/KEY: misc_feature
<222> LOCATION: (1)..(3933)
<223> OTHER INFORMATION: hypoxia-inducible factor 1 subunit alpha
      (HIF1-alpha)

<400> SEQUENCE: 59
cacgaggcag cactctcttc gtcgcttcgg ccagtgtgtc gggctgggcc ctgacaagcc      60
acctgaggag aggctcggag ccgggcccgg accccggcga ttgccgcccg cttctctcta    120
gtctcacgag gggtttcccg cctcgcaccc ccacctctgg acttgccttt ccttctcttc    180
tccgcgtgtg gagggagcca gcgcttaggc cggagcgagc ctgggggccg cccgccgtga    240
agacatcgcg gggaccgatt caccatggag gcgccggcg gcgcgaacga caagaaaaag    300
ataagttctg aacgtcgaaa agaaaagtct cgagatgcag ccagatctcg gcgaagtaaa    360
```

```
gaatctgaag ttttttatga gcttgctcat cagttgccac ttccacataa tgtgagttcg    420
catcttgata aggcctctgt gatgaggctt accatcagct atttgcgtgt gaggaaactt    480
ctggatgctg gtgatttgga tattgaagat gacatgaaag cacagatgaa ttgcttttat    540
ttgaaagcct tggatggttt tgttatggtt ctcacagatg atggtgacat gatttacatt    600
tctgataatg tgaacaaata catgggatta actcagtttg aactaactgg acacagtgtg    660
tttgatttta ctcatccatg tgaccatgag gaaatgagag aaatgcttac acacagaaat    720
ggccttgtga aaagggtaa agaacaaaac acacagcgaa gcttttttct cagaatgaag    780
tgtaccctaa ctagccgagg aagaactatg aacataaagt ctgcaacatg gaaggtattg    840
cactgcacag gccacattca cgtatatgat accaacagta accaacctca gtgtgggtat    900
aagaaaccac ctatgacctg cttggtgctg atttgtgaac ccattcctca cccatcaaat    960
attgaaattc ctttagatag caagactttc ctcagtcgac acagcctgga tatgaaattt   1020
tcttattgtg atgaaagaat taccgaattg atgggatatg agccagaaga acttttaggc   1080
cgctcaattt atgaatatta tcatgctttg gactctgatc atctgaccaa aactcatcat   1140
gatatgttta ctaaaggaca agtcaccaca ggacagtaca ggatgcttgc caaaagaggt   1200
ggatatgtct gggttgaaac tcaagcaact gtcatatata acaccaagaa ttctcaacca   1260
cagtgcattg tatgtgtgaa ttacgttgtg agtggtatta ttcagcacga cttgattttc   1320
tcccttcaac aaacagaatg tgtccttaaa ccggttgaat cttcagatat gaaaatgact   1380
cagctattca ccaaagttga atcagaagat acaagtagcc tctttgacaa acttaagaag   1440
gaacctgatg ctttaacttt gctggcccca gccgctggag acacaatcat atctttagat   1500
tttggcagca acgacacaga aactgatgac cagcaacttg aggaagtacc attatataat   1560
gatgtaatgc tcccctcacc caacgaaaaa ttacagaata taaatttggc aatgtctcca   1620
ttacccaccg ctgaaacgcc aaagccactt cgaagtagtc ctgaccctgc actcaatcaa   1680
gaagttgcat taaaattaga accaaatcca gagtcactgg aactttcttt taccatgccc   1740
cagattcagg atcagacacc tagtccttcc gatggaagca ctagacaaag ttcacctgag   1800
cctaatagtc ccagtgaata ttgttttttat gtggatagtg atatggtcaa tgaattcaag   1860
ttggaattgg tagaaaaact ttttgctgaa gacacagaag caaagaaccc attttctact   1920
caggacacag atttagactt ggagatgtta gctccctata tcccaatgga tgatgacttc   1980
cagttacgtt ccttcgatca gttgtcacca ttagaaagca gttccgcaag ccctgaaagc   2040
gcaagtcctc aaagcacagt tacagtattc cagcagactc aaatacaaga acctactgct   2100
aatgccacca ctaccactgc caccactgat gaattaaaaa cagtgacaaa agaccgtatg   2160
gaagacatta aatattgat tgcatctcca tctcctaccc acatacataa agaaactact   2220
agtgccacat catcaccata tagagatact caaagtcgga cagcctcacc aaacagagca   2280
ggaaaaggag tcatagaaca gacagaaaaa tctcatccaa gaagccctaa cgtgttatct   2340
gtcgctttga gtcaaagaac tacagttcct gaggaagaac taaatccaaa gatactagct   2400
ttgcagaatg ctcagagaaa gcgaaaaatg gaacatgatg gttcactttt tcaagcagta   2460
ggaattggaa cattattaca gcagccagac gatcatgcag ctactacatc actttcttgg   2520
aaacgtgtaa aaggatgcaa atctagtgaa cagaatggaa tggagcaaaa gacaattatt   2580 ttaatacccct ctgatttagc atgtagactc ctggggcaat caatggatga agtggattga   2640
ccacagctga ccagttatga ttgtgaagtt aatgctccta tacaaggcag cagaaaccta   2700
```

```
ctgcagggtg aagaattact cagagctttg gatcaagtta actgagcttt ttcttaattt      2760 cattccttt  tttggacact ggtggctcac tacctaaagc agtctattta tattttctac      2820
atctaatttt agaagcctgg ctacaatact gcacaaactt ggttagttca attttgatc       2880 cccttctac ttaatttaca ttaatgctct ttttagtat gttctttaat gctggatcac        2940
agacagctca ttttctcagt ttttggtat ttaaaccatt gcattgcagt agcatcattt       3000 taaaaatgc  acctttttat ttattattt ttggctaggg agtttatccc ttttcgaat        3060 tattttaag  aagatgccaa tataatttt gtaagaaggc agtaacctt catcatgatc        3120 ataggcagtt gaaaatttt tacacctttt ttttcacatt ttacataaat aataatgctt      3180
tgccagcagt acgtggtagc cacaattgca caatatattt tcttaaaaaa taccagcagt      3240
tactcatgga atatattctg cgtttataaa actagttttt aagaagaaat ttttttggc       3300 ctatgaaatt gttaaacctg aacatgaca ttgttaatca tataataatg attcttaaat       3360
gctgtatggt ttattattta aatgggtaaa gccatttaca taatatagaa agatatgcat      3420
atatctagaa ggtatgtggc atttatttgg ataaaattct caattcagag aaatcatctg      3480
atgtttctat agtcactttg ccagctcaaa agaaaacaat accctatgta gttgtggaag      3540
tttatgctaa tattgtgtaa ctgatattaa acctaaatgt tctgcctacc ctgttggtat      3600
aaagatattt tgagcagact gtaaacaaga aaaaaaaat catgcattct tagcaaaatt       3660
gcctagtatg ttaatttgct caaaatacaa tgtttgattt tatgcacttt gtcgctatta      3720 acatccttt  tttcatgtag atttcaataa ttgagtaatt ttagaagcat tattttagga      3780
atatatagtt gtcacagtaa atatcttgtt ttttctatgt acattgtaca aatttttcat      3840
tccttttgct ctttgtggtt ggatctaaca ctaactgtat tgttttgtta catcaaataa      3900
acatcttctg tggaaaaaaa aaaaaaaaaa aaa                                   3933
```

<210> SEQ ID NO 60
<211> LENGTH: 3166
<212> TYPE: DNA
<213> ORGANISM: Homo sapiens
<220> FEATURE:
<221> NAME/KEY: misc_feature
<222> LOCATION: (1)..(3166)
<223> OTHER INFORMATION: VEGF A

<400> SEQUENCE: 60

```
aagagctcca gagagaagtc gaggaagaga gagacggggt cagagagagc gcgcgggcgt        60
gcgagcagcg aaagcgacag gggcaaagtg agtgacctgc ttttgggggt gaccgccgga      120
gcgcggcgtg agccctcccc cttgggatcc cgcagctgac cagtcgcgct gacggacaga      180
cagacagaca ccgcccccag ccccagttac cacctcctcc ccggccggcg gcggacagtg      240
gacgcggcgg cgagccgcgg gcaggggccg gagcccgccc ccggaggcgg ggtggagggg      300 gtcgagctc  gcgcgtcgc actgaaactt ttcgtccaac ttctgggctg ttctcgcttc       360
ggaggagccg tggtccgcgc gggggaagcc gagccgagcg gagccgcgag aagtgctagc      420
tcgggccggg aggagccgca gccggaggag ggggaggagg aagaagagaa ggaagaggag      480
agggggccgc agtggcgact cggcgctcgg aagccgggct catggacggg tgaggcggcg      540
gtgtgcgcag acagtgctcc agcgcgcgcg ctccccagcc ctggcccggc ctcgggccgg      600
gaggaagagt agctcgccga ggcgccgagg agagcgggcc gccccacagc ccgagccgga      660
gagggacgcg agccgcgcgc cccggtcggg cctccgaaac catgaacttt ctgctgtctt      720
gggtgcattg gagccttgcc ttgctgctct acctccacca tgccaagtgg tcccaggctg      780
```

-continued

```
cacccatggc agaaggagga gggcagaatc atcacgaagt ggtgaagttc atggatgtct      840
atcagcgcag ctactgccat ccaatcgaga ccctggtgga catcttccag gagtaccctg      900
atgagatcga gtacatcttc aagccatcct gtgtgcccct gatgcgatgc gggggctgct      960
ccaatgacga gggcctggag tgtgtgccca ctgaggagtc caacatcacc atgcagatta     1020
tgcggatcaa acctcaccaa ggccagcaca taggagagat gagcttccta cagcacaaca     1080
aatgtgaatg cagaccaaag aaagatagag caagacaaga aaatccctgt gggccttgct     1140
cagagcggag aaagcatttg tttgtacaag atccgcagac gtgtaaatgt tcctgcaaaa     1200
acacacactc gcgttgcaag gcgaggcagc ttgagttaaa cgaacgtact tgcagatgtg     1260
acaagccgag gcggtgagcc gggcaggagg aaggagcctc cctcagggtt tcgggaacca     1320
gatctctctc caggaaagac tgatacagaa cgatcgatac agaaaccacg ctgccgccac     1380
cacaccatca ccatcgacag aacagtcctt aatccagaaa cctgaaatga aggaagagga     1440
gactctgcgc agagcacttt gggtccggag ggcgagactc cggcggaagc attcccgggc     1500
gggtgaccca gcacggtccc tcttggaatt ggattcgcca ttttattttt cttgctgcta     1560
aatcaccgag cccggaagat tagagagttt tatttctggg attcctgtag acacacccac     1620
ccacatacat acatttatat atatatatat tatatatata taaaaataaa tatctctatt     1680
ttatatatat aaaatatata tattcttttt ttaaattaac agtgctaatg ttattggtgt     1740
cttcactgga tgtatttgac tgctgtggac ttgagttggg aggggaatgt tcccactcag     1800
atcctgacag ggaagaggag gagatgagag actctggcat gatcttttttt ttgtcccact     1860
tggtggggcc agggtcctct cccctgccca agaatgtgca aggccagggc atggggggcaa    1920
atatgaccca gttttgggaa caccgacaaa cccagccctg gcgctgagcc tctctacccc     1980
aggtcagacg gacagaaaga caaatcacag gttccgggat gaggacaccg gctctgacca     2040
ggagtttggg gagcttcagg acattgctgt gctttgggga ttccctccac atgctgcacg     2100
cgcatctcgc ccccaggggc actgcctgga agattcagga gcctgggcgg ccttcgctta     2160
ctctcacctg cttctgagtt gcccaggagg ccactggcag atgtcccggc gaagagaaga     2220
gacacattgt tggaagaagc agcccatgac agcgccccctt cctgggactc gccctcatcc     2280
tcttcctgct ccccttcctg gggtgcagcc taaaaggacc tatgtcctca ccaccattgaa    2340
accactagtt ctgtcccccc aggaaacctg gttgtgtgtg tgtgagtggt tgaccttcct     2400
ccatcccctg gtccttccct tcccttcccg aggcacagag agacagggca ggatccacgt     2460
gcccattgtg gaggcagaga aaagagaaag tgttttatat acggtactta tttaatatcc     2520
cttttttaatt agaaattaga acagttaatt taattaaaga gtagggtttt ttttcagtat    2580
tcttggttaa tatttaattt caactattta tgagatgtat cttttgctct ctcttgctct     2640
cttatttgta ccggttttttg tatataaaat tcatgtttcc aatctctctc tccctgatcg    2700
gtgacagtca ctagcttatc ttgaacagat atttaatttt gctaacactc agctctgccc     2760
tccccgatcc cctggctccc cagcacacat tcctttgaaa gagggtttca atatacatct     2820
acatactata tatatattgg gcaacttgta tttgtgtgta tatatatata tatatgttta     2880
tgtatatatg tgatcctgaa aaaataaaca tcgctattct gttttttata tgttcaaacc     2940
aaacaagaaa aaatagagaa ttctacatac taaatctctc tccttttttta attttaatat   3000
ttgttatcat ttatttattg gtgctactgt ttatccgtaa taattgtggg gaaaagatat     3060
taacatcacg tctttgtctc tagtgcagtt tttcgagata ttccgtagta catatttatt     3120
```

-continued tttaaacaac gacaaagaaa tacagatata tcttaaaaaa aaaaaa                  3166

<210> SEQ ID NO 61
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: sequence stemming from wild human p53

<400> SEQUENCE: 61
gaggtgcgtg tttgtgc                                                  17

<210> SEQ ID NO 62
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: sequence stemming from wild human p53

<400> SEQUENCE: 62
gcatgaaccg gaggcccat                                                19

<210> SEQ ID NO 63
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: sequence stemming from wild human p53

<400> SEQUENCE: 63
gcatgaaccg gaggcccat                                                19

<210> SEQ ID NO 64
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: sequence stemming from wild human p53

<400> SEQUENCE: 64
gcatgaaccg gaggcccat                                                19

<210> SEQ ID NO 65
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: sequence stemming from wild human p53

<400> SEQUENCE: 65
ctgcatgggc ggcatgaac                                                19

<210> SEQ ID NO 66

-continued

```
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: sequence stemming from wild human p53

<400> SEQUENCE: 66
tgggagagac cggcgcaca                                               19

<210> SEQ ID NO 67
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: sequence stemming from wild human p53

<400> SEQUENCE: 67
tgtgaggcac tgcccccac                                               19

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: sequence stemming from wild human p53

<400> SEQUENCE: 68
taacagttcc tgcatgggcg                                              20

<210> SEQ ID NO 69
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: sequence stemming from the human mutated gene
      p53 bearing the mutation r273h

<400> SEQUENCE: 69
gaggtgcatg tttgtgc                                                 17

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: sequence stemming from the human mutated gene
      p53 bearing the mutation r248q

<400> SEQUENCE: 70
gcatgaacca gaggcccat                                               19

<210> SEQ ID NO 71
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: sequence stemming from the human mutated gene
      p53 bearing the mutation r248w

<400> SEQUENCE: 71
gcatgaactg gaggccat                                                18

<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: sequence stemming from the human mutated gene
      p53 bearing the mutation r249s

<400> SEQUENCE: 72
gcatgaaccg gagtcccat                                               19

<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: sequence stemming from the human mutated gene
      p53 bearing the mutation g245s

<400> SEQUENCE: 73
ctgcatgggc agcatgaac                                               19

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: sequence stemming from the human mutated gene
      p53 bearing the mutation r282w

<400> SEQUENCE: 74
tgggagagac tggcgcaca                                               19

<210> SEQ ID NO 75
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: sequence stemming from the human mutated gene
      p53 bearing the mutation r175h

<400> SEQUENCE: 75
tgtgaggcgc tgcccccac                                               19

<210> SEQ ID NO 76
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: sequence stemming from the human mutated gene
      p53 bearing the mutation c242s

<400> SEQUENCE: 76
taacagttcc tccatgggcg                                                  20

<210> SEQ ID NO 77
<211> LENGTH: 3231
<212> TYPE: DNA
<213> ORGANISM: Homo sapiens
<220> FEATURE:
<223> OTHER INFORMATION: androgen receptor

<400> SEQUENCE: 77
agctagctgc agcgactacc gcatcatcac agcctgttga actcttctga gcaagagaag         60
gggaggcggg gtaagggaag taggtggaag attcagccaa gctcaaggat ggaagtgcag        120
ttagggctgg gaagggtcta ccctcggccg ccgtccaaga cctaccgagg agctttccag        180
aatctgttcc agagcgtccg cgaagtgatc cagaacccgg gccccaggca cccagaggcc        240
gcgagcgcag cacctcccgg cgccagtttg ctgctgctgc agcagcagca gcagcagcag        300
cagcagcagc agcagcagca gcagcaagag actagcccca ggcagcagca gcagcagcag        360
ggtgaggatg gttctcccca agcccatcgt agaggcccca caggctacct ggtcctggat        420
gaggaacagc aaccttcaca gccgcagtcg gccctggagt gccaccccga gagaggttgc        480
gtcccagagc ctggagccgc cgtggccgcc agcaaggggc tgccgcagca gctgccagca        540
cctccggacg aggatgactc agctgcccca tccacgttgt ccctgctggg ccccactttc        600
cccggcttaa gcagctgctc cgctgacctt aaagacatcc tgagcgaggc cagcaccatg        660
caactccttc agcaacagca gcaggaagca gtatccgaag gcagcagcag cgggagagcg        720
agggaggcct cgggggctcc cacttcctcc aaggacaatt acttaggggg cacttcgacc        780
atttctgaca cgccaagga gttgtgtaag gcagtgtcgg tgtccatggg cctgggtgtg         840
gaggcgttgg agcatctgag tccaggggaa cagcttcggg gggattgcat gtacgcccca        900
cttttgggag ttccacccgc tgtgcgtccc actccttgtg ccccattggc cgaatgcaaa        960
ggttctctgc tagacgacag cgcaggcaag agcactgaag atactgctga gtattcccct       1020
ttcaagggag gttacaccaa agggctagaa ggcgagagcc taggctgctc tggcagcgct       1080
gcagcaggga ctccgggac acttgaactg ccgtctaccc tgtctctcta caagtccgga       1140
gcactggacg aggcagctgc gtaccagagt cgcgactact acaactttcc actggctctg       1200 gccgaccgc cgccccctcc gccgcctccc catccccacg ctcgcatcaa gctggagaac       1260
ccgctggact acggcagcgc ctgggcggct gcggcggcgc agtgccgcta tgggacctg       1320 gcgagcctgc atggcgcggg tgcagcggga cccggttctg ggtcaccctc agccgccgct       1380
tcctcatcct ggcacactct cttcacagcc gaagaaggcc agttgtatgg accgtgtggt       1440
ggtggtgggg gtggtggcgg cggcggcggc ggcggcggcg gcggcgaggc gggagctgta       1500
gccccctacg gctacactcg gccccctcag gggctggcgg gccaggaaag cgacttcacc       1560
gcacctgatg tgtggtaccc tggcggcatg gtgagcagag tgcccataccc cagtcccact       1620 tgtgtcaaaa gcgaaatggg cccctggatg gatagctact ccggacctta cggggacatg       1680
```

```
cgtttggaga ctgccaggga ccatgttttg cccattgact attactttcc accccagaag    1740
acctgcctga tctgtggaga tgaagcttct gggtgtcact atggagctct cacatgtgga    1800
agctgcaagg tcttcttcaa aagagccgct gaagggaaac agaagtacct gtgcgccagc    1860
agaaatgatt gcactattga taaattccga aggaaaaatt gtccatcttg tcgtcttcgg    1920
aaatgttatg aagcagggat gactctggga gcccggaagc tgaagaaact tggtaatctg    1980
aaactacagg aggaaggaga ggcttccagc accaccagcc ccactgagga gacaacccag    2040
aagctgacag tgtcacacat tgaaggctat gaatgtcagc ccatctttct gaatgtcctg    2100
gaagccattg agccaggtgt agtgtgtgct ggacacgaca acaaccagcc cgactccttt    2160
gcagccttgc tctctagcct caatgaactg ggagagagac agcttgtaca cgtggtcaag    2220
tgggccaagg ccttgcctgg cctccgcaac ttacacgtgg acgaccagat ggctgtcatt    2280
cagtactcct ggatggggct catggtgttt gccatgggct ggcgatcctt caccaatgtc    2340
aactccagga tgctctactt cgcccctgat ctggttttca atgagtaccg catgcacaag    2400
tcccggatgt acagccagtg tgtccgaatg aggcacctct ctcaagagtt tggatggctc    2460
caaatcaccc cccaggaatt cctgtgcatg aaagccatgc tactcttcag cattattcca    2520
gtggatgggc tgaaaaatca aaaattcttt gatgaacttc gaatgaacta catcaaggaa    2580
ctcgatcgta tcattgcatg caaaagaaaa aatcccacat cctgctcaag acgcttctac    2640
cagctcacca agctcctgga ctccgtgcag cctattgcga gagagctgca tcagttcact    2700
tttgacctgc taatcaagtc acacatggtg agcgtggact ttccggaaat gatggcagag    2760
atcatctctg tgcaagtgcc caagatcctt tctgggaaag tcaagcccat ctatttccac    2820
acccagtgaa gcattggaaa ccctatttcc ccaccccagc tcatgccccc tttcagatgt    2880
cttctgcctg ttataactct gcactactcc tctgcagtgc cttggggaat ttcctctatt    2940
gatgtacagt ctgtcatgaa catgttcctg aattctatct gctgggcttt ttttttctct    3000
ttctctcctt tcttttctt cttccctccc tatctaaccc tcccatggca ccttcagact    3060
ttgcttccca ttgtggctcc tatctgtgtt ttgaatggtg ttgtatgcct taaatctgtg    3120
atgatcctca tatggcccag tgtcaagttg tgcttgttta cacgcatctc tgtgccagcc    3180
acacaaaccg tttacttact taccgcaagg gaacttagag agctagaatt c            3231
```

The invention claimed is:

1. A method of treating prostate cancer comprising:
administering a therapeutically effective amount of a pharmaceutical composition having at least one double stranded oligonucleotide comprising two complementary oligonucleotide sequences forming a hybrid, wherein each oligonucleotide sequence comprises at one of their 3' or 5' ends one to five unpaired nucleotides forming single-strand ends extending beyond the hybrid, and wherein said at least one double stranded oligonucleotide is selected from the group consisting of a hybrid of two complementary oligonucleotide sequences consisting of SEQ ID NO:15 and SEQ ID NO:16 and a hybrid of two complementary oligonucleotide sequences consisting of SEQ ID NO:19 and SEQ ID NO:20.

* * * * *